United States Patent
Yang et al.

(10) Patent No.: US 11,161,828 B2
(45) Date of Patent: Nov. 2, 2021

(54) CLASS OF BISQUATERNARY AMMONIUM COMPOUND AS WELL AS THE PREPARATIVE METHOD AND THE USE THEREOF

(71) Applicant: WEST CHINA HOSPITAL, SICHUAN UNIVERSITY, Sichuan (CN)

(72) Inventors: Jun Yang, Sichuan (CN); Jin Liu, Sichuan (CN); Weiyi Zhang, Sichuan (CN); Wensheng Zhang, Sichuan (CN); Cheng Zhou, Sichuan (CN); Bowen Ke, Sichuan (CN); Lei Tang, Sichuan (CN)

(73) Assignee: WEST CHINA HOSPITAL, SICHUAN UNIVERSITY, Sichuan (CN)

( * ) Notice: Subject to any disclaimer, the term of this patent is extended or adjusted under 35 U.S.C. 154(b) by 0 days.

(21) Appl. No.: 17/044,158

(22) PCT Filed: Jul. 24, 2019

(86) PCT No.: PCT/CN2019/097506
§ 371 (c)(1),
(2) Date: Sep. 30, 2020

(87) PCT Pub. No.: WO2020/020231
PCT Pub. Date: Jan. 30, 2020

(65) Prior Publication Data
US 2021/0155598 A1   May 27, 2021

(30) Foreign Application Priority Data
Jul. 25, 2018   (CN) .......................... 201810828371.7

(51) Int. Cl.
*C07D 295/15* (2006.01)
*A61P 21/02* (2006.01)

(52) U.S. Cl.
CPC ............ *C07D 295/15* (2013.01); *A61P 21/02* (2018.01)

(58) Field of Classification Search
CPC ..................................................... C07D 295/15
See application file for complete search history.

(56) References Cited

U.S. PATENT DOCUMENTS

2011/0082113 A1   4/2011   Hynes et al.

FOREIGN PATENT DOCUMENTS

| CN | 101392014 A | 3/2009 |
| CN | 101588803 A | 11/2009 |
| CN | 108250143 A | 7/2018 |
| CN | 108727248 A | 11/2018 |

OTHER PUBLICATIONS

Zhang, Can et al.; Synthesis and Neuromuscular Blocking Activity of Bis-[(1-benzyl) tetrahydroisoquinoline] Quaternary Ammonium Compounds; Journal of China Pharmaceutical University; vol. 32, No. 6, Dec. 31, 2001, pp. 403-407.

*Primary Examiner* — Shawquia Jackson
(74) *Attorney, Agent, or Firm* — Novick, Kim & Lee, PLLC; Allen Xue

(57) ABSTRACT

A two-quaternary ammonium compound has a structural formula of formula (I). L1 is a C1 to C8 alkylene group; L2 is a C1 to C8 alkylene group; Z1 is nitro group or a halogen or methoxy group; Z2 is nitro group or a halogen or methoxy group; Z3 is nitro group or a halogen or methoxy group; R=H or a C1 to C6 alkyl group; a, b, and c are independently an integer from 0-5; and M is a pharmaceutically acceptable anion, such as a bromine ion, chlorine ion, sulfonate radical, etc. A stereoisomer or mixture of stereoisomers, or a pharmaceutically acceptable salt or solvate or eutectic of the compound of formula (I) forms a composition with a pharmaceutically acceptable carrier, or forms a compounded prescription with other active components, and the composition or compounded prescription may be used in the preparation of a muscle relaxant.

10 Claims, No Drawings

CLASS OF BISQUATERNARY AMMONIUM COMPOUND AS WELL AS THE PREPARATIVE METHOD AND THE USE THEREOF

TECHNICAL FIELD

The present invention belongs to the field of drug synthesis, and specifically relates to a class of bisquaternary ammonium compounds as well as the preparative method and the use thereof.

BACKGROUND ART

During surgical anesthesia, neuromuscular blockers (also known as muscle relaxants) can produce muscle relaxation and are used to relax skeletal muscles during surgery and tracheal intubation. The above-mentioned muscle relaxants are classified into depolarization and non-depolarization types according to their action mechanism, and can be divided into four categories: ultra-short-acting, short-acting, medium-acting and long-acting according to their duration of action (Anesthesiology, 82(1), 33a, 1995).

Among depolarizing muscle relaxants, only succinylcholine is still used in clinical. Due to its special action mechanism, succinylcholine has serious side effects, such as elevated blood potassium, malignant hyperthermia, arrhythmia, increased intraocular pressure, and gastric tension, etc. The advantage of succinylcholine is that it has a short action time, such as it lasts for 10 minutes and has a rapid effect in the human body, and thus it is used as an ultra-short-acting muscle relaxant in clinical practice. Its feature is particularly suitable for emergency treatment, because in emergency situations, using muscle relaxants with longer acting time may cause severe brain damage and even death. At present, the depolarizing muscle relaxant succinylcholine is the most suitable muscle relaxant for emergency.

In addition to not having ultra-short-acting effects, non-depolarizing muscle relaxants are considered as safer muscle relaxants. Clinicians have been seeking for non-depolarizing muscle relaxants with ultra-short-actions (Anesthesia and Analgsia, 61(9), 721, 1982; Current opinion in anesthesiology, 8, 362, 1995). However, all non-depolarizing muscle relaxants currently used in clinical do not have ultra-short-acting characteristics (meaning the muscle relaxant duration <10 min after single dose). For example, after single administration, the duration of muscle relaxation for micuronium is 15-20 min, while the action times for cisatracurium and rocuronium are 40-60 minutes, but the action time of pancuronium is longer than 60 min. CN101588803A discloses a non-depolarizing muscle relaxant, and cysteine at 200× the dose of the drug can be administrated to quickly reverse its muscle relaxant effect. Although the rapid regression of muscle relaxant is achieved, a large amount of sulfhydryl amino acids (such as semi-cystine) must be used, which will obviously increase medical procedures, and a large number of sulfhydryl amino acids will also increase uncertainty in safety, such as excessive cysteine results in tracheal spasm and vomiting. Therefore, the ultra-short-acting and non-depolarizing muscle relaxants that do not require reversal agents are more meet the clinical needs, and can reduce the economic burden of patients, increase the safety of patient, reduce operations of medical personnels, and save medical resources.

Content of the Invention

The object of the present invention is to provide a class of bisquaternary ammonium compounds as well as the preparative method and the use thereof.

The present invention first provides a bisquaternary ammonium compound, having the structure of formula (I):

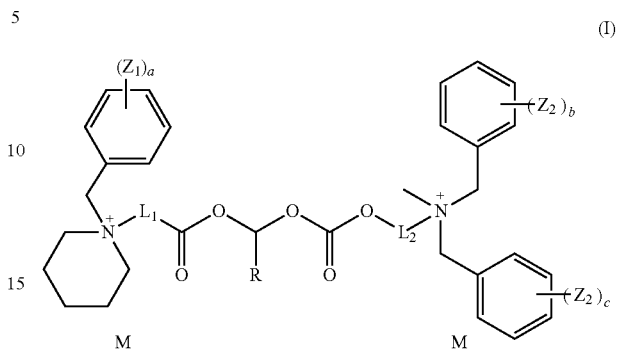

Wherein, $L_1$ is $C_1$-$C_8$ alkylenyl; $L_2$ is $C_1$-$C_8$ alkylenyl; $Z_1$ is nitro or halogen or methoxyl; $Z_2$ is nitro or halogen or methoxyl; $Z_3$ is nitro or halogen or methoxyl; R=H or $C_1$-$C_6$ alkyl; a, b, and c are independently an integer of 0-5; M is a pharmaceutically acceptable anion, such as bromide, chloride, sulfonate, etc.

Further, $Z_1$, $Z_2$, and $Z_3$ are fluorine; a, b, and c are independently an integer of 0-5.

Further, $Z_1$, $Z_2$, and $Z_3$ are chlorine; a, b, and c are independently an integer of 0-2.

Further, $Z_1$, $Z_2$, and $Z_3$ are nitro; a, b, and c are independently an integer of 0-2.

Further, $Z_1$, $Z_2$, and $Z_3$ are bromine; a, b, and c are independently an integer of 0-2.

Further, $Z_1$, $Z_2$, and $Z_3$ are methoxyl; a, b, and c are independently an integer of 0-2.

Further, R is H or methyl.

Further, said compound is one of the following compounds:

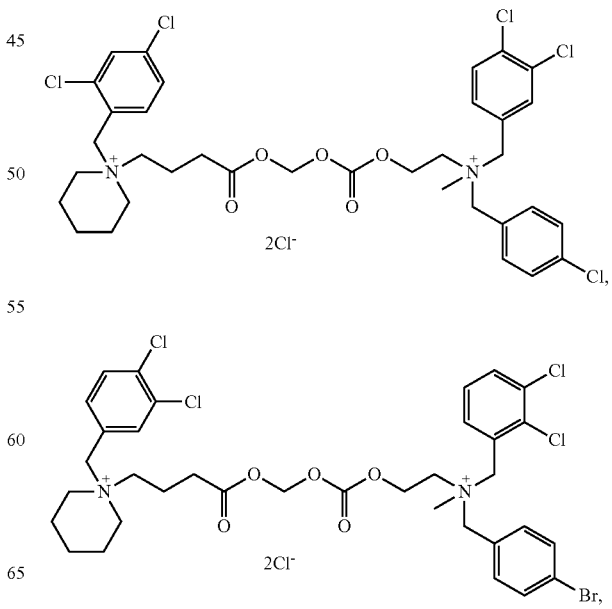

3
-continued
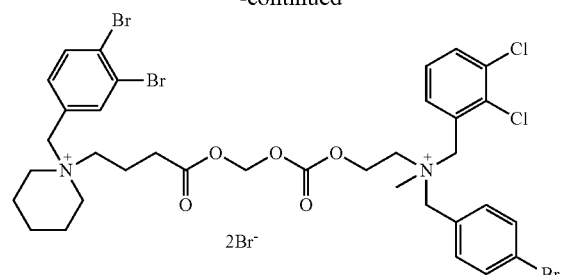
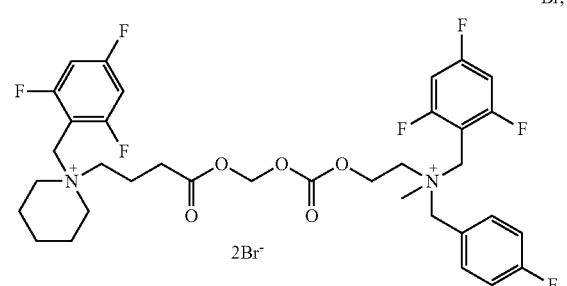
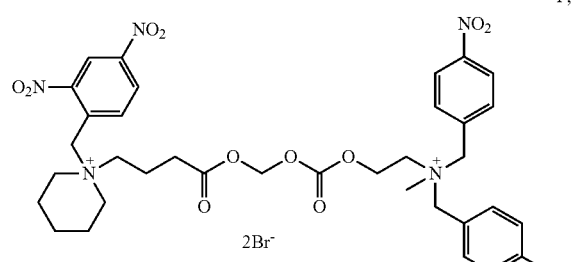
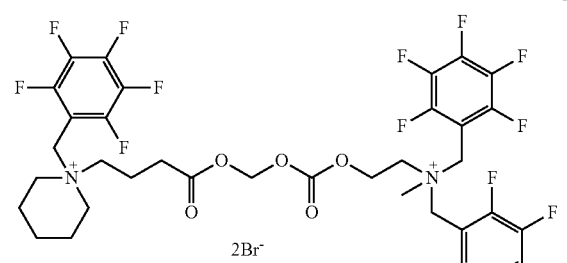
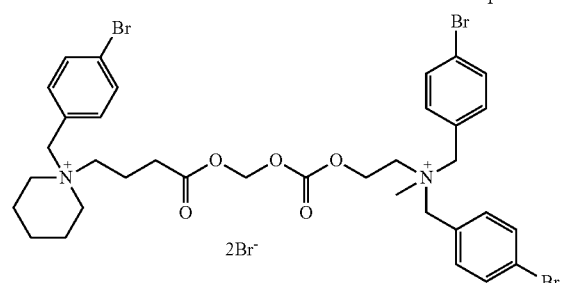
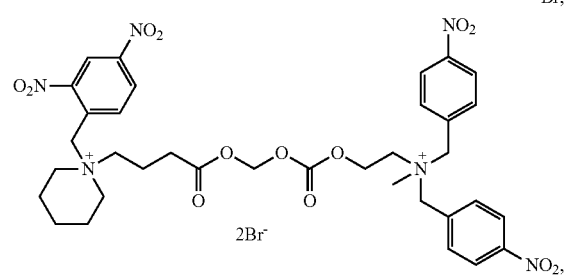
4
-continued
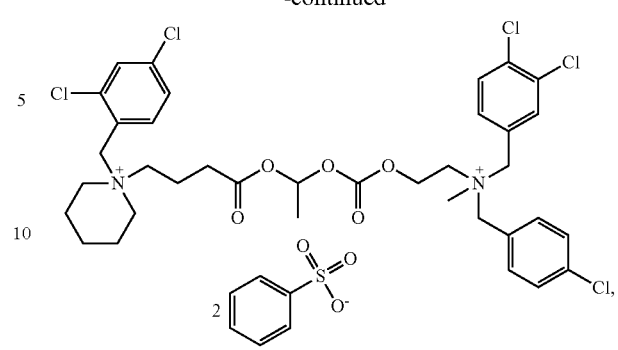
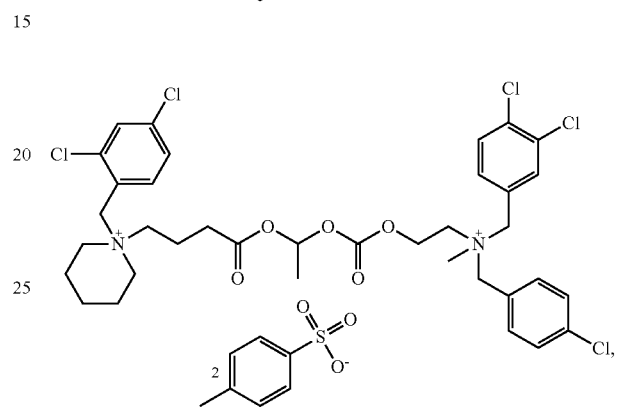
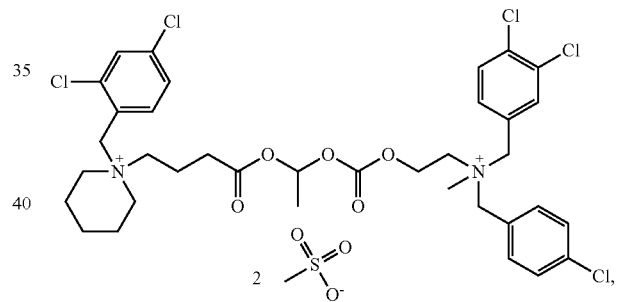
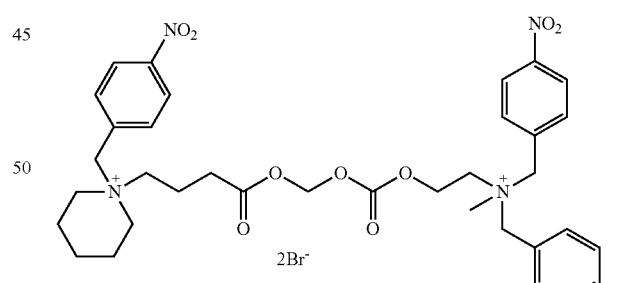
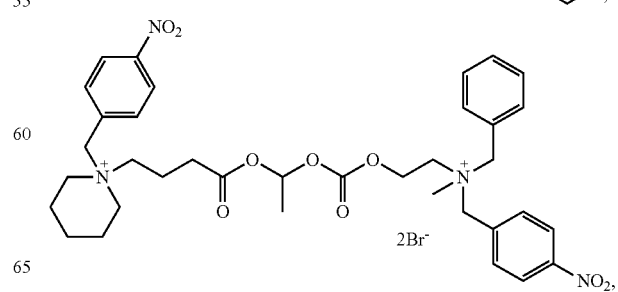

-continued
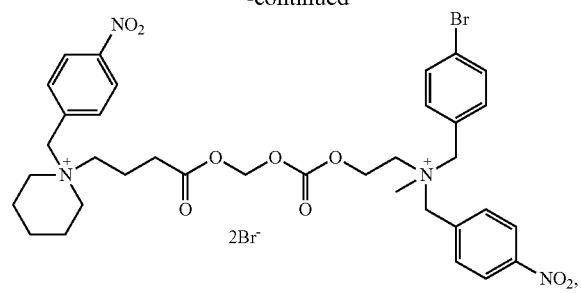
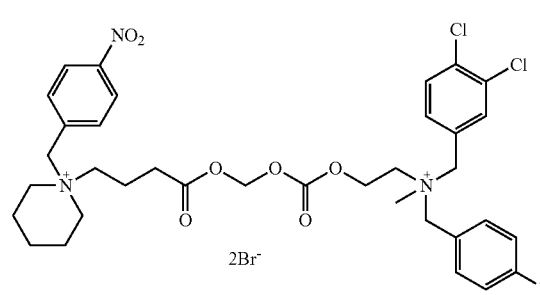
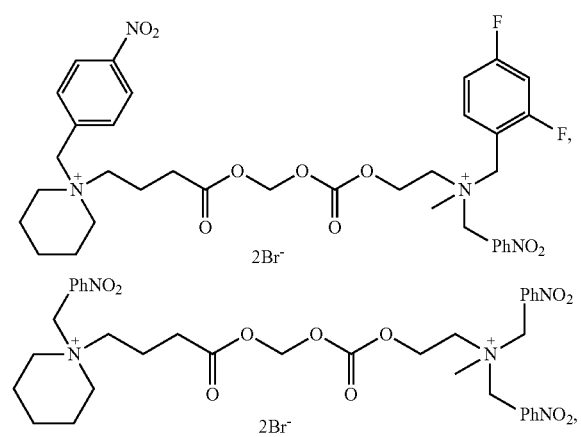
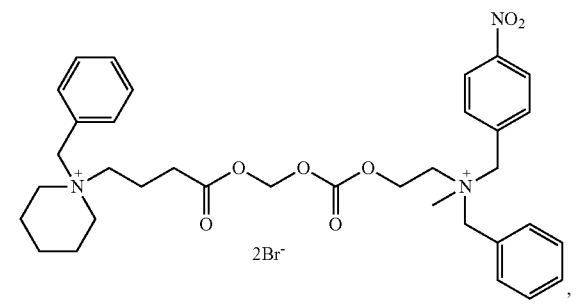
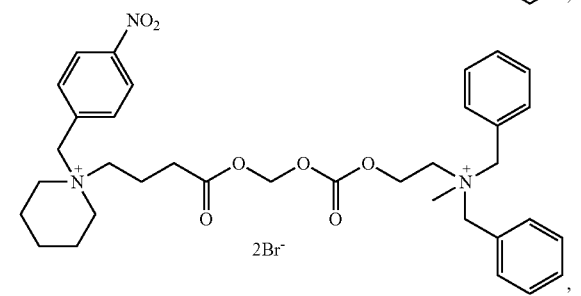
-continued
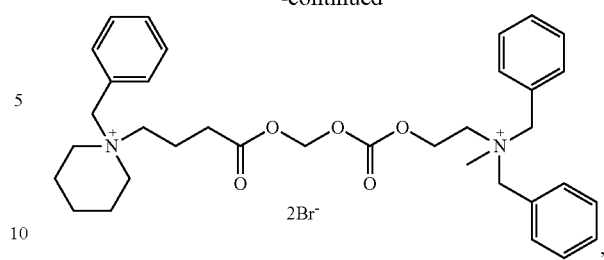
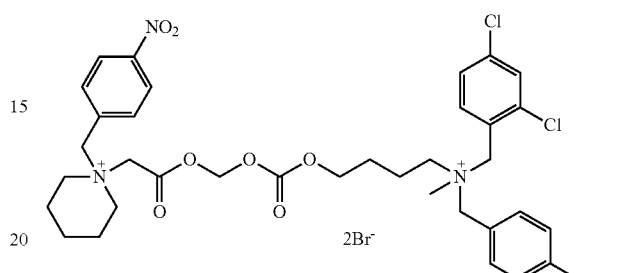
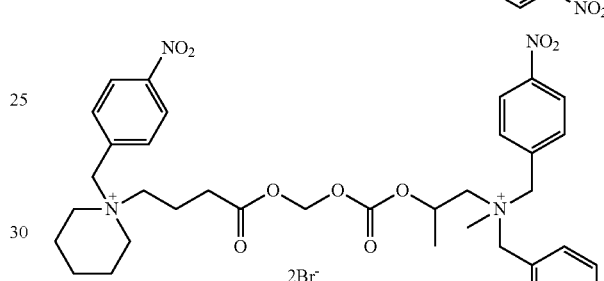
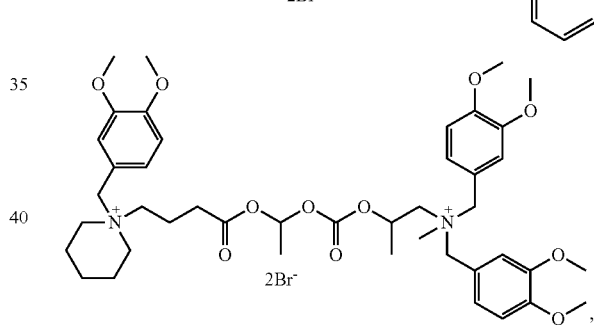
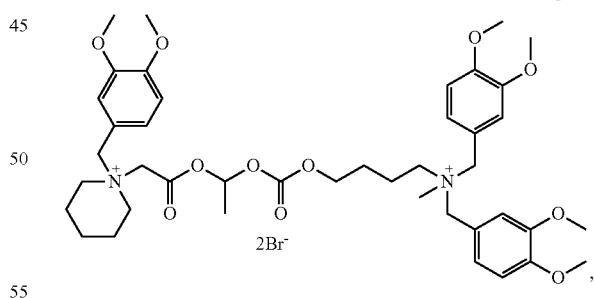
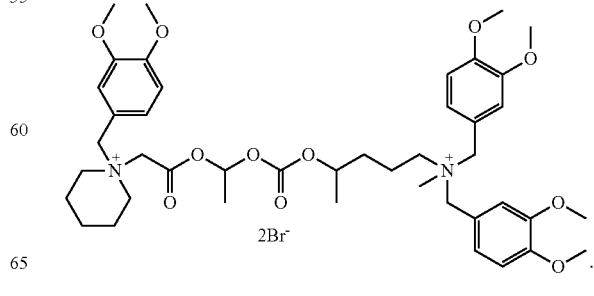

The present invention further provides the use of bisquaternary ammonium compound mentioned above in the preparation of muscle relaxants.

The present invention further provides a muscle relaxant, which is prepared using the bisquaternary ammonium compound according to anyone of claims 1-8 as active ingredients, with the addition of pharmaceutically acceptable adjuvants.

The compound of formula (I) has a rapid effect after single administration, and provides 2-10 min of complete muscle relaxation. These compounds only need to rely on the body's own metabolism, and can achieve ultra-short-acting non-depolarizing muscle relaxation. After exerting ultra-short-acting effect on muscle relaxation, it is cleared up quickly by itself.

Based on above-mentioned characteristics, compounds with the structure of formula (I), the stereoisomers or the mixtures of stereoisomers, or the pharmaceutically acceptable salts, or the solvates or the co-crystals and the combinations thereof, and their combinations with pharmaceutically acceptable can be used in the field of preparation of muscle relaxants, to provide fast, ultra-short-acting, and non-depolarizing muscle relaxant and meet the clinical needs.

For the definition of term used in the present invention: unless otherwise specified, the initial definition provided for the group or the term herein is applicable to those in the whole specification; for terms not specifically defined herein, according to the disclosure content and the context, the term should have the meaning commonly given by those skilled in the field.

The minimum and maximum values of carbon atom content in the hydrocarbon group are indicated by a prefix, for example, the prefix $(C_a\text{-}C_b)$alkyl indicates any alkyl group having "a"-"b" carbon atoms. Therefore, for example, $(C_1\text{-}C_6)$ alkyl means an alkyl containing 1-6 carbon atoms.

$C_1\text{-}C_6$ alkyl denotes $C_1$, $C_2$, $C_3$, $C_4$, $C_5$, $C_6$ alkyl, that is linear or branched alkyl having 1-6 carbon atoms, such as methyl, ethyl, propyl, isopropyl, butyl, isobutyl, tert-butyl, sec-butyl, pentyl, hexyl, etc.

$C_1\text{-}C_8$ alkylenyl denotes methylidene, ethylidene, propylidene, butylidene, pentylidene, hexylidene and the like.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

Example 1 Preparation of Compound 1

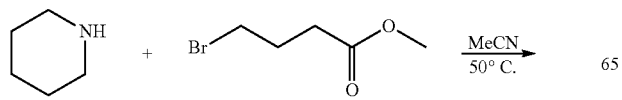

-continued

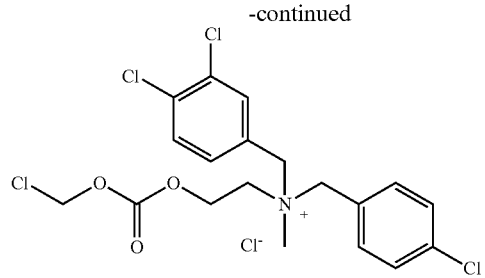

1-2

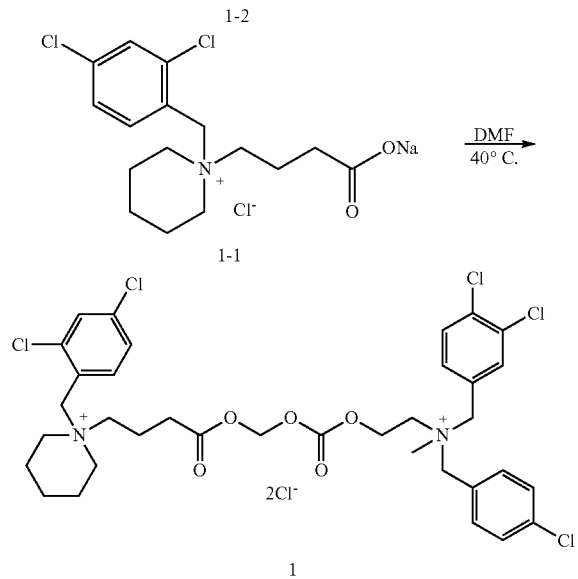

Methyl 4-bromobutyrate (1.81 g) was dissolved in 30 mL acetonitrile, to which were added 0.85 g piperidine and 1.38 g anhydrous potassium carbonate. The reaction was stirred at 50° C. for 10 h, and then 2,4-dichlorobenzyl chloride (1.95 g) was added. The mixture was stirred at 75° C. for 6 h, filtered, and evaporated under reduced pressure to remove the solvent. 2N sodium hydroxide aqueous solution (40 mL) was added to the residue, and the mixture was stirred at room temperature for 2 h. Then, the pH value was adjusted to 9 with 2N dilute hydrochloric acid, and the solvent was evaporated under reduced pressure. 50 ml dichloromethane was added to the residue, and the mixture was heated to almost boiling, then filtered while hot. The filtrate was evaporated to obtain 2.67 g crude product as bright yellow intermediate 1-1.

Hydroxyethyl-4-chlorobenzyl-methylamine (1.99 g) was dissolved in 30 mL acetonitrile, to which was added 3,4-dichlorobenzyl chloride (1.95 g). The mixture was stirred at 75° C. for 8 h, and then the solvent was evaporated under reduced pressure, to precipitate yellow solid. The solid was dissolved in 50 mL dichloromethane, to which was added 1.6 g pyridine. The reaction was cooled to 5° C., and chloromethyl chloroformate (1.3 g) was drop added. After addition, the mixture was stirred for 3 h at room temperature. The solvent was evaporated under reduced pressure, and the residue was purified by column chromatography to provide 2.72 g intermediate (1-2).

1.94 g intermediate 1-1 and 2.44 g intermediate 1-2 were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (0.93 g), i.e. compound 1, with a yield of 22.7%.

$^1$HNMR (400 MHz, DMSO-$d_6$) δ: 1.41-1.47 (1H, m), 1.61-1.64 (1H, m), 1.78-1.89 (4H, m), 2.03-2.12 (2H, m), 2.54-2.59 (2H, m), 3.10 (3H, s), 3.15-3.26 (4H, m), 3.42-3.44 (2H, m), 3.65-3.74 (2H, m), 4.66-4.75 (6H, m), 4.87-4.98 (2H, m), 5.78 (2H, s), 7.43-7.52 (8H, m), 7.62-7.73 (2H, m).

Example 2 Preparation of Compound 2

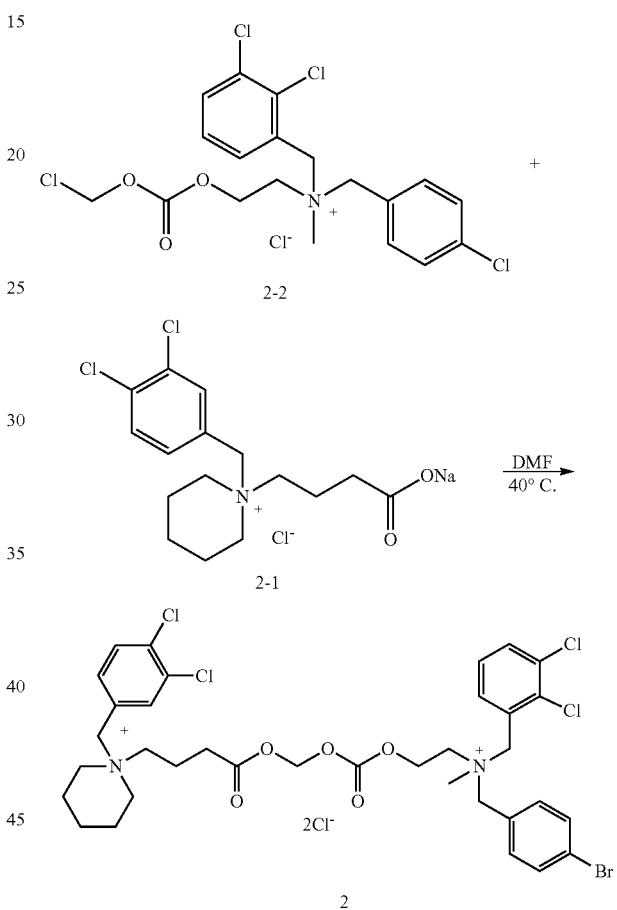

Intermediates 2-1 and 2-2 can be prepared by referring to the preparative method of the intermediate in Example 1. Intermediate 2-1 (1.99 g) and intermediate 2-2 (2.44 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (1.02 g), i.e. compound 2, with a yield of 23.7%.

$^1$HNMR (400 MHz, DMSO-$d_6$) δ: 1.42-1.48 (1H, m), 1.63-1.66 (1H, m), 1.78-1.89 (4H, m), 2.04-2.14 (2H, m), 2.56-2.61 (2H, m), 3.08 (3H, s), 3.15-3.26 (4H, m), 3.41-3.45 (2H, m), 3.64-3.75 (2H, m), 4.65-4.77 (6H, m), 4.86-4.95 (2H, m), 5.75 (2H, s), 7.40-7.49 (6H, m), 7.52-7.83 (4H, m).

Example 3 Preparation of Compound 3

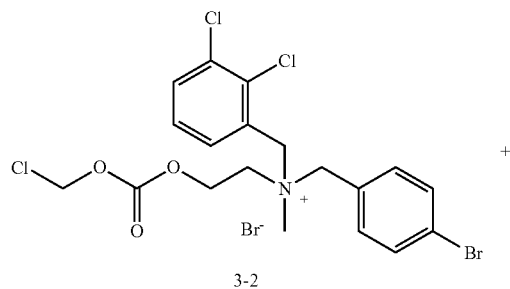
3-2

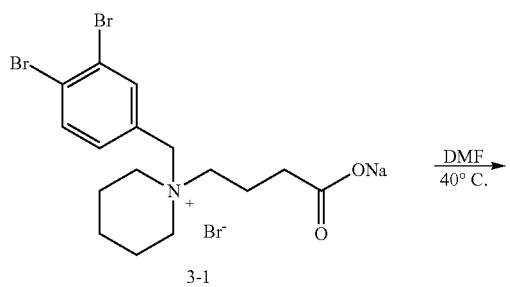
3-1

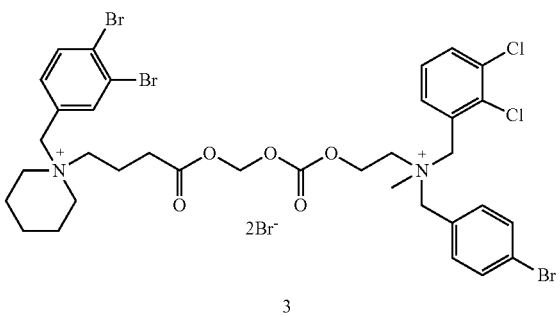
3

Intermediates 3-1 and 3-2 can be prepared by referring to the preparative method of the intermediate in Example 1. In order to ensure that the anion is Br⁻, benzyl bromide reagent and hydrobromic acid were used to replace benzyl chloride reagent and dilute hydrochloric acid in Example 1 when preparing intermediates 3-1 and 3-2. Intermediate 3-1 (2.61 g) and intermediate 3-2 (2.88 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (1.07 g), i.e. compound 3, with a yield of 24.3%.

$^1$HNMR (400 MHz, DMSO-$d_6$) δ: 1.41-1.46 (1H, m), 1.62-1.67 (1H, m), 1.78-1.89 (4H, m), 2.03-2.13 (2H, m), 2.56-2.61 (2H, m), 3.05 (3H, s), 3.15-3.26 (4H, m), 3.41-3.45 (2H, m), 3.64-3.75 (2H, m), 4.65-4.77 (6H, m), 4.86-4.95 (2H, m), 5.75 (2H, s), 7.39-7.48 (6H, m), 7.53-7.82 (4H, m).

Example 4 Preparation of Compound 4

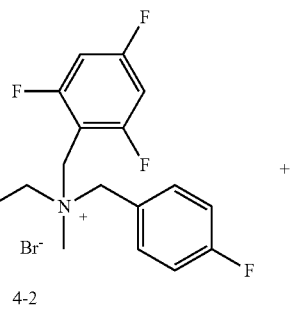
4-2

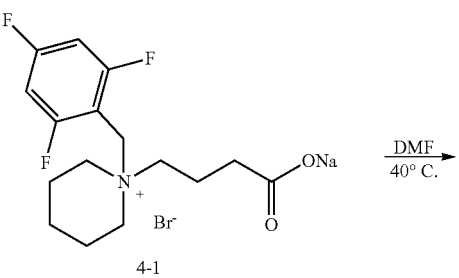
4-1

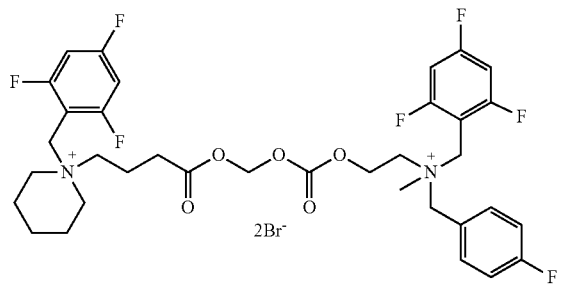
4

Intermediates 4-1 and 4-2 can be prepared by referring to the preparative method of the intermediate in Example 1. In order to ensure that the anion is Br⁻, benzyl bromide reagent and hydrobromic acid were used to replace benzyl chloride reagent and dilute hydrochloric acid in Example 1 when preparing intermediates 4-1 and 4-2. Intermediate 4-1 (2.09 g) and intermediate 4-2 (2.51 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (1.31 g), i.e. compound 4, with a yield of 30.5%.

$^1$HNMR (400 MHz, DMSO-$d_6$) δ: 1.40-1.43 (1H, m), 1.62-1.65 (1H, m), 1.77-1.88 (4H, m), 2.05-2.15 (2H, m), 2.55-2.60 (2H, m), 3.07 (3H, s), 3.15-3.26 (4H, m), 3.42-3.46 (2H, m), 3.63-3.75 (2H, m), 4.64-4.77 (6H, m), 4.85-4.95 (2H, m), 5.74 (2H, s), 7.26-7.37 (4H, m), 7.42-7.49 (4H, m).

Example 5 Preparation of Compound 5

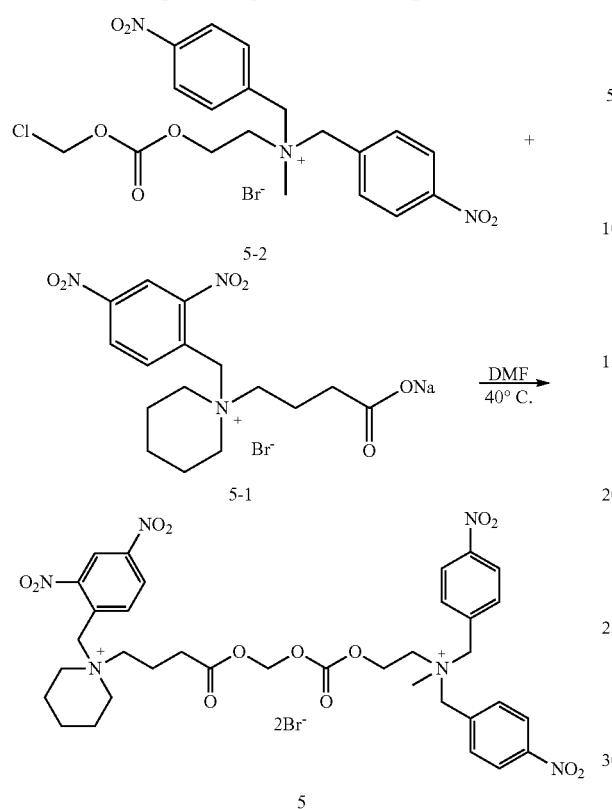

Intermediates 5-1 and 5-2 can be prepared by referring to the preparative method of the intermediate in Example 1. In order to ensure that the anion is Br', benzyl bromide reagent and hydrobromic acid were used to replace benzyl chloride reagent and dilute hydrochloric acid in Example 1 when preparing intermediates 5-1 and 5-2. Intermediate 5-1 (2.27 g) and intermediate 5-2 (2.59 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (1.28 g), i.e. compound 5, with a yield of 28.0%.

$^1$HNMR (400 MHz, DMSO-d$_6$) δ: 1.41-1.43 (1H, m), 1.62-1.64 (1H, m), 1.77-1.88 (4H, m), 2.04-2.15 (2H, m), 2.54-2.60 (2H, m), 3.03 (3H, s), 3.14-3.26 (4H, m), 3.41-3.46 (2H, m), 3.63-3.76 (2H, m), 4.63-4.77 (6H, m), 4.85-4.95 (2H, m), 5.76 (2H, s), 7.65-7.97 (5H, m), 8.37-8.86 (6H, m).

Example 6 Preparation of Compound 6

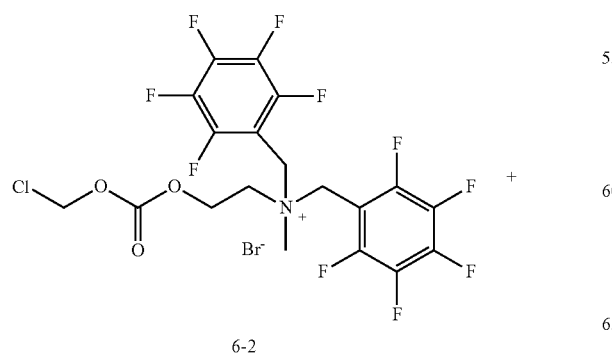

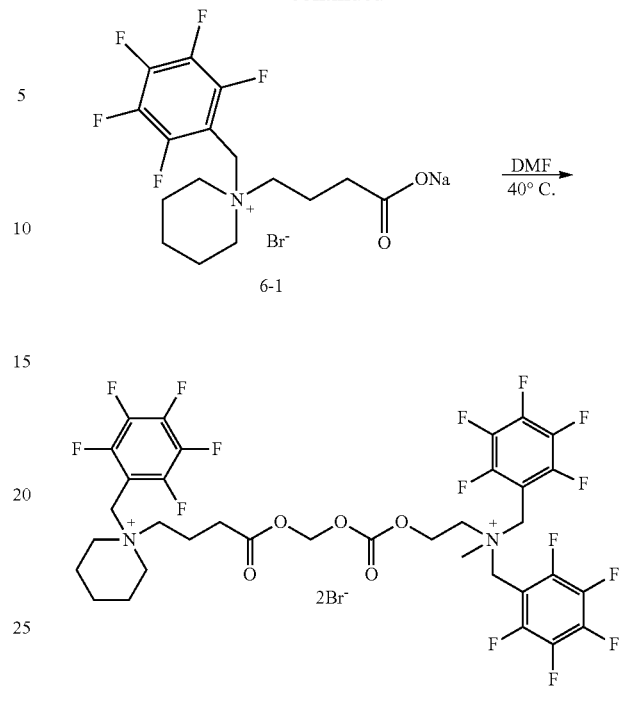

Intermediates 6-1 and 6-2 can be prepared by referring to the preparative method of the intermediate in Example 1. In order to ensure that the anion is Br', benzyl bromide reagent and hydrobromic acid were used to replace benzyl chloride reagent and dilute hydrochloric acid in Example 1 when preparing intermediates 6-1 and 6-2. Intermediate 6-1 (2.27 g) and intermediate 6-2 (3.04 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (1.56 g), i.e. compound 6, with a yield of 31.1%.

$^1$HNMR (400 MHz, DMSO-d$_6$) δ: 1.40-1.45 (1H, m), 1.61-1.64 (1H, m), 1.75-1.86 (4H, m), 2.05-2.16 (2H, m), 2.53-2.59 (2H, m), 3.08 (3H, s), 3.13-3.25 (4H, m), 3.40-3.45 (2H, m), 3.62-3.77 (2H, m), 4.62-4.77 (6H, m), 4.85-4.95 (2H, m), 5.78 (2H, s).

Example 7 Preparation of Compound 7

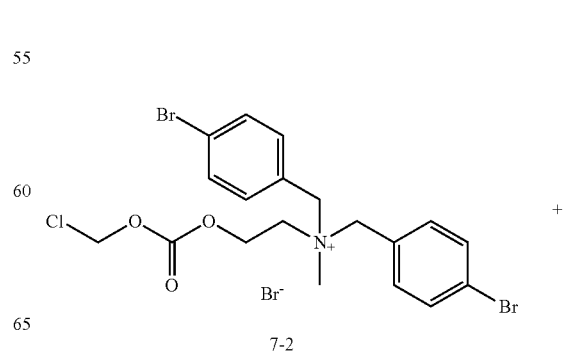

-continued

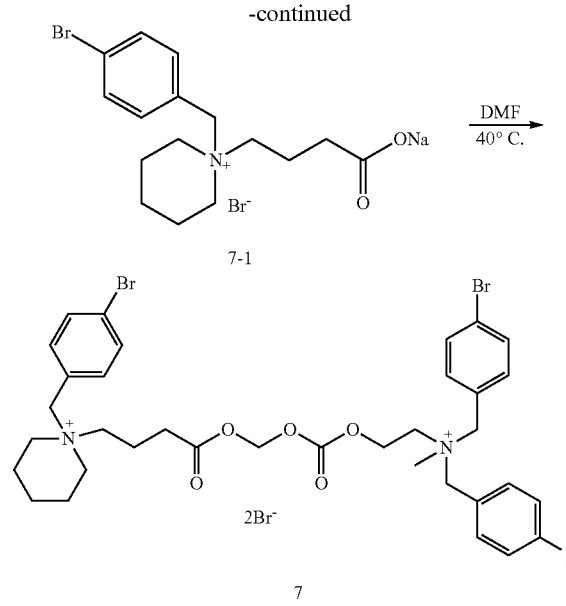

-continued

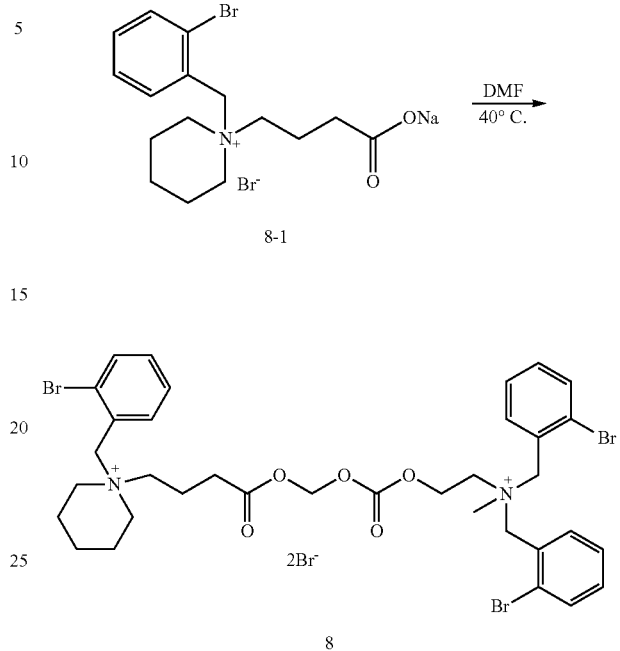

Intermediates 7-1 and 7-2 can be prepared by referring to the preparative method of the intermediate in Example 1. In order to ensure that the anion is Br⁻, benzyl bromide reagent and hydrobromic acid were used to replace benzyl chloride reagent and dilute hydrochloric acid in Example 1 when preparing intermediates 7-1 and 7-2. Intermediate 7-1 (2.22 g) and intermediate 7-2 (2.93 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (1.16 g), i.e. compound 7, with a yield of 23.9%.

¹HNMR (400 MHz, DMSO-d$_6$) δ: 1.41-1.46 (1H, m), 1.62-1.65 (1H, m), 1.78-1.89 (4H, m), 2.05-2.16 (2H, m), 2.55-2.61 (2H, m), 3.07 (3H, s), 3.15-3.26 (4H, m), 3.41-3.45 (2H, m), 3.64-3.75 (2H, m), 4.65-4.77 (6H, m), 4.86-4.95 (2H, m), 5.75 (2H, s), 7.43-7.49 (6H, m), 7.54-7.88 (6H, m).

Example 8 Preparation of Compound 8

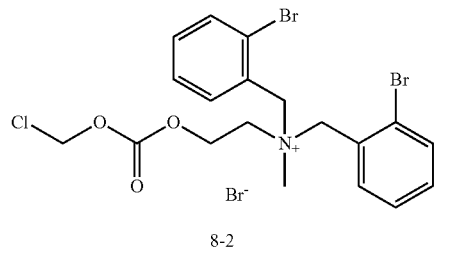

Intermediates 8-1 and 8-2 can be prepared by referring to the preparative method of the intermediate in Example 1. In order to ensure that the anion is Br', benzyl bromide reagent and hydrobromic acid were used to replace benzyl chloride reagent and dilute hydrochloric acid in Example 1 when preparing intermediates 8-1 and 8-2. Intermediate 8-1 (2.22 g) and intermediate 8-2 (2.93 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (0.85 g), i.e. compound 8, with a yield of 17.5%.

¹HNMR (400 MHz, DMSO-d$_6$) δ: 1.40-1.44 (1H, m), 1.62-1.67 (1H, m), 1.78-1.89 (4H, m), 2.03-2.13 (2H, m), 2.56-2.61 (2H, m), 3.05 (3H, s), 3.15-3.26 (4H, m), 3.41-3.45 (2H, m), 3.64-3.75 (2H, m), 4.65-4.77 (6H, m), 4.86-4.95 (2H, m), 5.75 (2H, s), 7.39-7.48 (6H, m), 7.53-7.82 (6H, m).

Example 9 Preparation of Compound 9

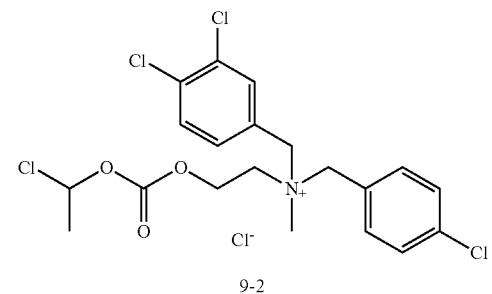

+

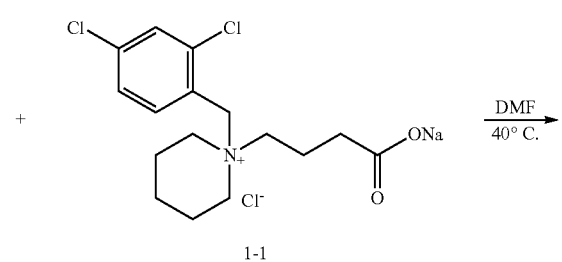

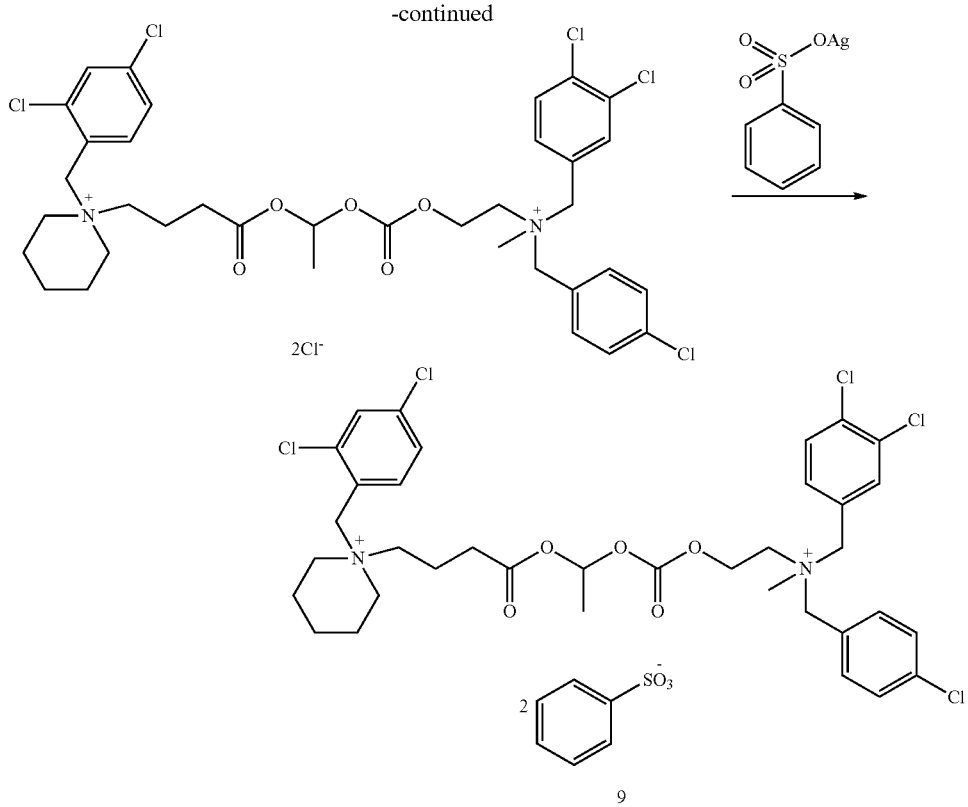

Intermediates 1-1 and 9-2 can be prepared by referring to the preparative method of the intermediate in Example 1. Intermediates 1-1 (3.88 g) and 9-2 (4.99 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (1.85 g). Then, 40 mL DMF and 20 mL water were added, followed by addition of 6 g silver toluenesulfonate. The mixture was stirred at room temperature for 2 h to precipitate the silver salt, then filtered, and the filtrate was evaporated under reduced pressure. The residue was separated by reversed-phase preparative chromatography to obtain 0.87 g white powder, i.e. compound 9, with a yield of 7.9%.

$^1$HNMR (400 MHz, MeOD) δ 1.54-1.65 (4H, m), 1.78-1.85 (1H, m), 1.98-2.10 (4H, m), 2.22-2.25 (2H, m), 2.59-2.60 (2H, m), 3.12-3.32 (4H, m), 3.37-3.61 (6H, m), 3.76-3.81 (3H, m), 4.67-4.99 (6H, m), 6.81-6.84 (1H, m), 7.43-7.52 (8H, m), 7.62-7.73 (2H, m), 7.75-7.81 (10H, m).

Example 10 Preparation of Compound 10

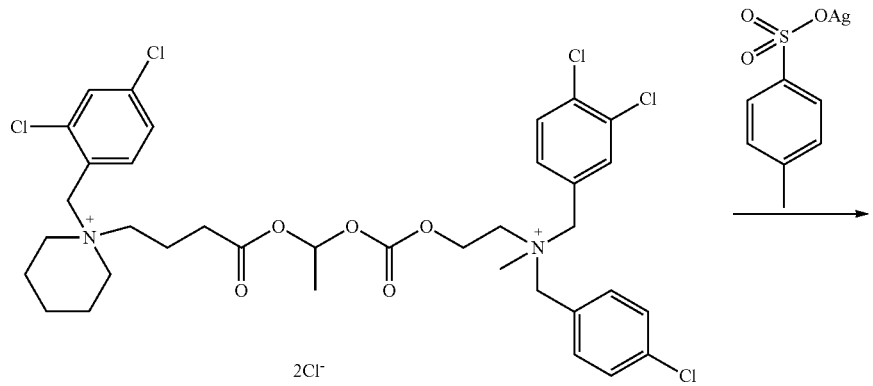

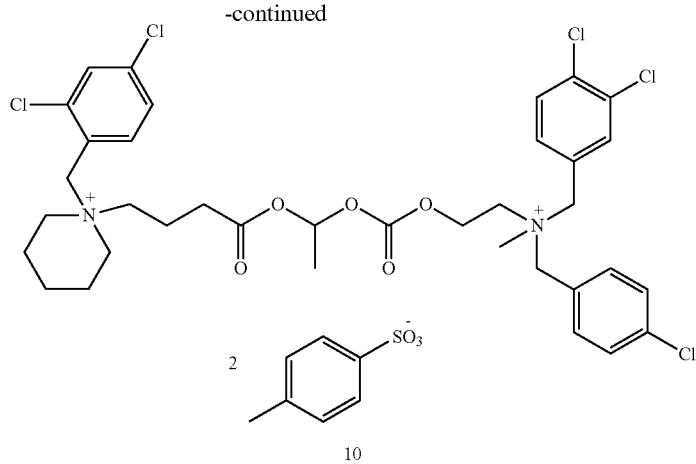
Referring to Example 9, compound 10 can be prepared by using silver p-toluenesulfonate in the step of precipitating silver salt.
¹HNMR (400 MHz, MeOD) δ: 1.53-1.65 (4H, m), 1.77-1.85 (1H, m), 1.97-2.10 (4H, m), 2.21-2.24 (2H, m), 2.43 (3H, s), 2.45 (3H, s), 2.59-2.60 (2H, m), 3.11-3.32 (4H, m), 3.38-3.61 (6H, m), 3.75-3.81 (3H, m), 4.68-4.99 (6H, m), 6.80-6.84 (1H, m), 7.41-7.52 (12H, m), 7.61-7.73 (6H, m).
Example 11 Preparation of Compound 11
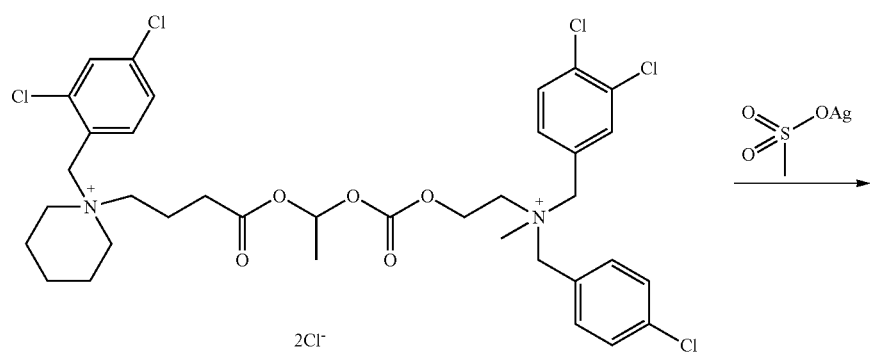
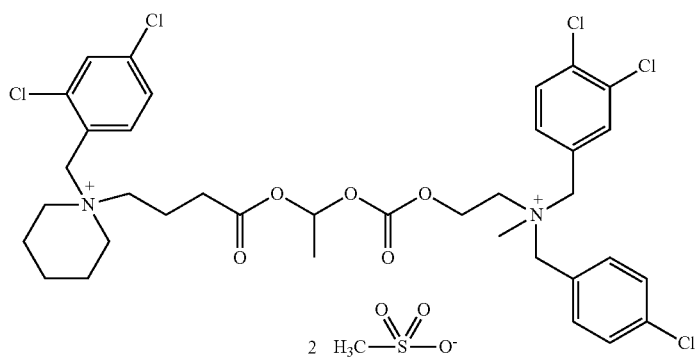

Referring to Example 9, compound 11 can be prepared by using silver methanesulphonate in the step of precipitating silver salt.

$^{1}$HNMR (400 MHz, MeOD) δ: 1.50-1.65 (4H, m), 1.74-1.85 (1H, m), 1.95-2.10 (4H, m), 2.20-2.24 (2H, m), 2.56-2.60 (2H, m), 2.83 (3H, s), 2.85 (3H, s), 3.11-3.32 (4H, m), 3.38-3.61 (6H, m), 3.74-3.81 (3H, m), 4.67-4.99 (6H, m), 6.80-6.85 (1H, m), 7.41-7.53 (8H, m), 7.61-7.74 (2H, m).

Example 12 Preparation of Compound 12

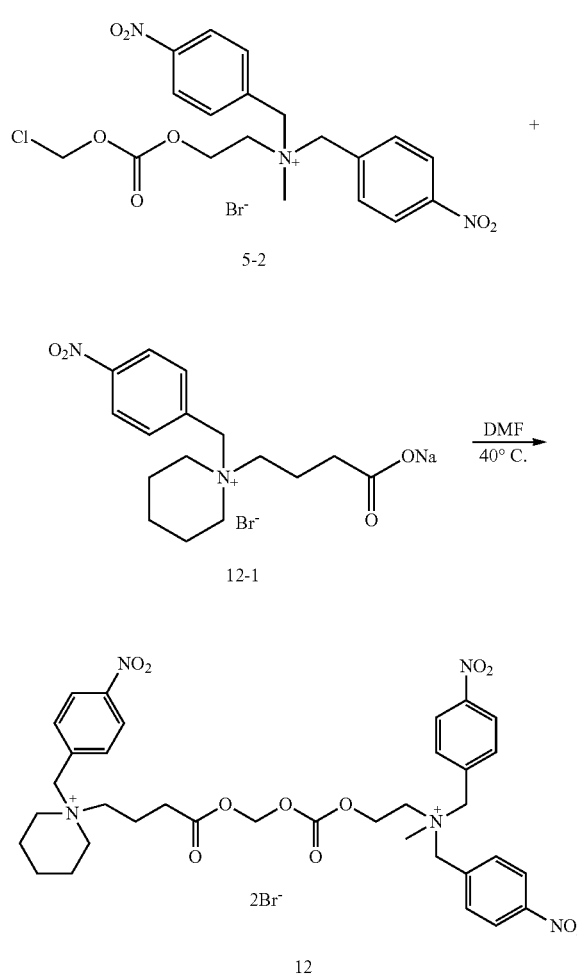

Intermediates 12-1 and 5-2 can be prepared by referring to the preparative method of the intermediate in Example 1. In order to ensure that the anion is Br', benzyl bromide reagent and hydrobromic acid were used to replace benzyl chloride reagent and dilute hydrochloric acid in Example 1 when preparing intermediates 12-1 and 5-2. Intermediate 12-1 (2.04 g) and intermediate 5-2 (2.59 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (1.08 g), i.e. compound 12, with a yield of 24.8%.

$^{1}$HNMR (400 MHz, DMSO-d$_6$) δ: 1.41-1.43 (1H, m), 1.59-1.61 (1H, m), 1.84 (4H, s, broad), 2.08-2.09 (2H, m), 2.57-2.60 (2H, m), 3.10 (3H, s), 3.25-3.49 (6H, m), 3.73 (2H, s), 4.72-4.77 (6H, m), 5.08 (2H, s), 5.78 (2H, s), 7.85-7.87 (2H, m), 7.94-7.95 (4H, m), 8.32-8.38 (6H, m).

Example 13 Preparation of Compound 13

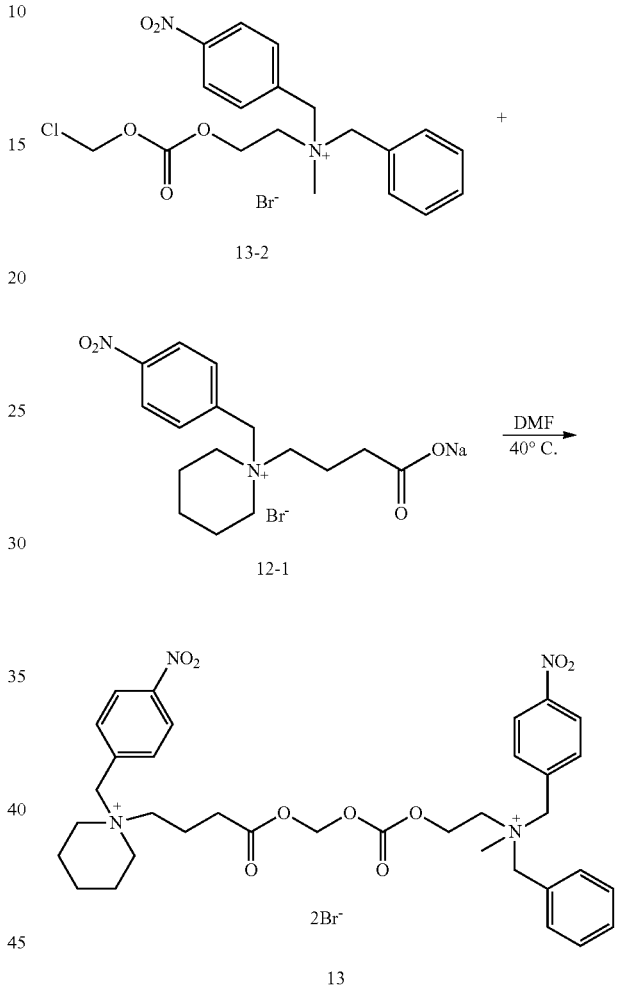

Intermediates 12-1 and 13-2 can be prepared by referring to the preparative method of the intermediate in Example 1. In order to ensure that the anion is Br, benzyl bromide reagent and hydrobromic acid were used to replace benzyl chloride reagent and dilute hydrochloric acid in Example 1 when preparing intermediates 12-1 and 13-2. Intermediate 12-1 (2.04 g) and intermediate 13-2 (2.36 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (1.08 g), i.e. compound 13, with a yield of 24.8%.

$^{1}$HNMR (400 MHz, DMSO-d$_6$) δ: 1.40-1.46 (1H, m), 1.60-1.63 (1H, m), 1.79-1.90 (4H, m), 2.04-2.12 (2H, m), 2.55-2.59 (2H, m), 3.03 (3H, s), 3.16-3.27 (4H, m), 3.41-3.43 (2H, m), 3.66-3.75 (2H, m), 4.67-4.76 (6H, m), 4.86-4.97 (2H, m), 5.77 (2H, s), 7.50-7.56 (3H, m), 7.60-7.62 (2H, m), 7.83-7.95 (4H, m), 8.31-8.37 (4H, m).

Example 14 Preparation of Compound 14

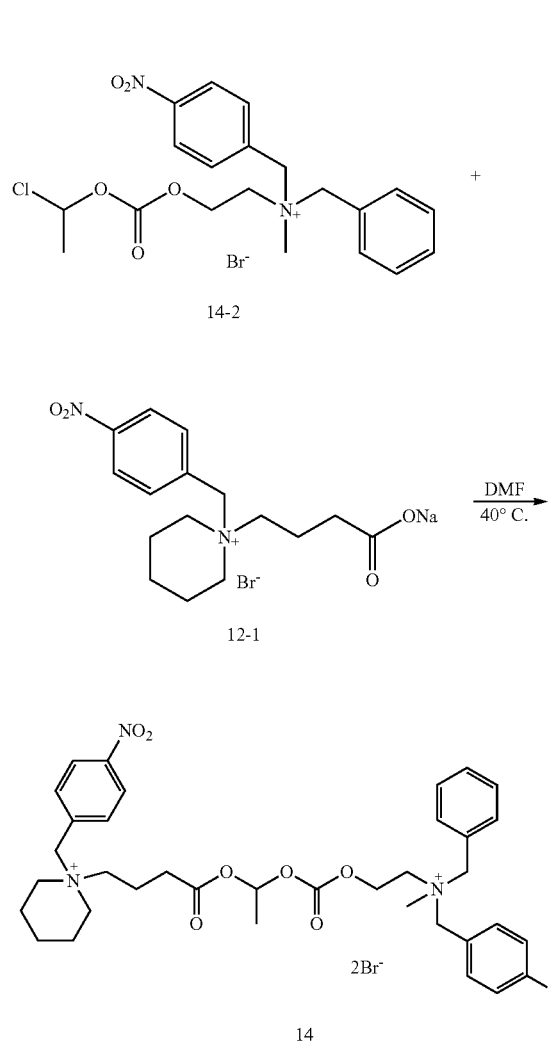

Example 15 Preparation of Compound 15

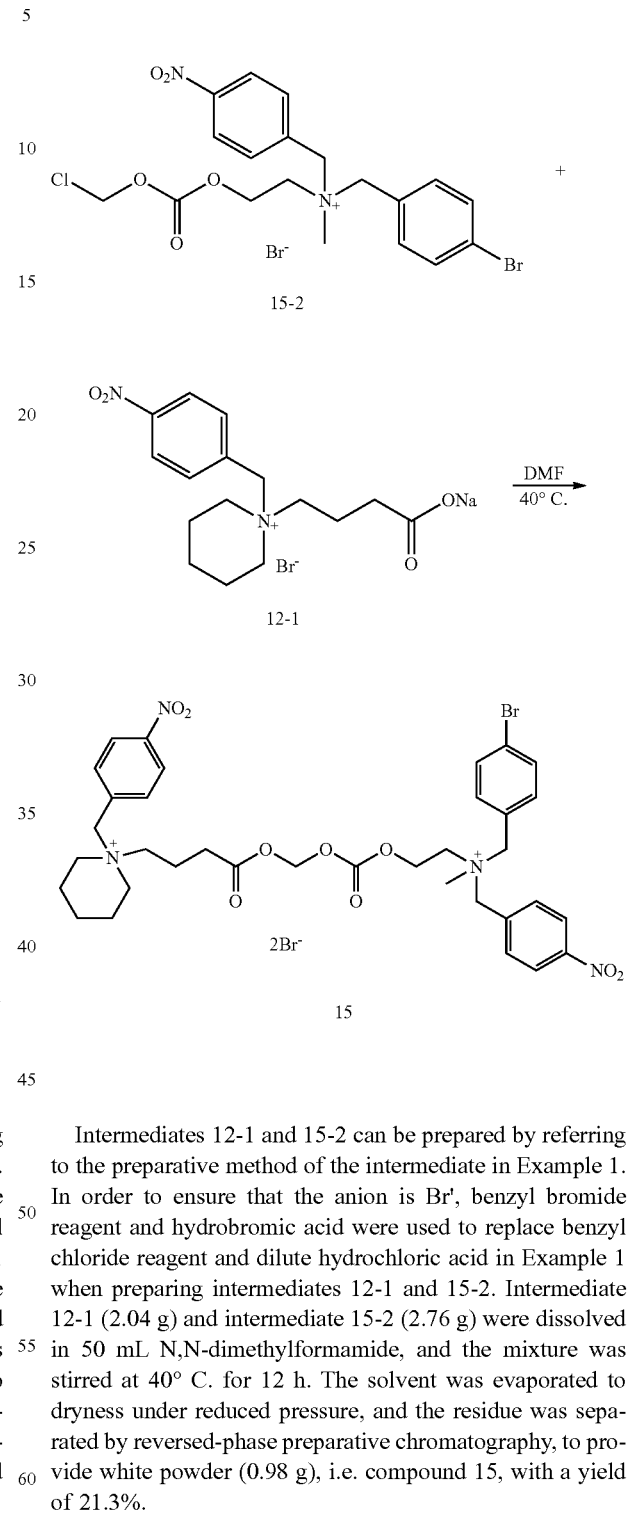

Intermediates 12-1 and 14-2 can be prepared by referring to the preparative method of the intermediate in Example 1. In order to ensure that the anion is Br⁻, benzyl bromide reagent and hydrobromic acid were used to replace benzyl chloride reagent and dilute hydrochloric acid in Example 1 when preparing intermediates 12-1 and 14-2. Intermediate 12-1 (2.04 g) and intermediate 14-2 (2.43 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (0.68 g), i.e. compound 14, with a yield of 16.2%.

$^1$HNMR (400 MHz, MeOD) δ 1.52-1.64 (4H, m), 1.77-1.85 (1H, m), 1.97-2.09 (4H, m), 2.21-2.24 (2H, m), 2.58-2.60 (2H, m), 3.11-3.32 (4H, m), 3.35-3.61 (6H, m), 3.75-3.81 (3H, m), 4.67-4.98 (6H, m), 6.80-6.84 (1H, m), 7.55-7.62 (5H, m), 7.82-7.95 (4H, m), 8.33-8.39 (4H, m).

Intermediates 12-1 and 15-2 can be prepared by referring to the preparative method of the intermediate in Example 1. In order to ensure that the anion is Br', benzyl bromide reagent and hydrobromic acid were used to replace benzyl chloride reagent and dilute hydrochloric acid in Example 1 when preparing intermediates 12-1 and 15-2. Intermediate 12-1 (2.04 g) and intermediate 15-2 (2.76 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (0.98 g), i.e. compound 15, with a yield of 21.3%.

$^1$HNMR (400 MHz, DMSO-d$_6$) δ: 1.43 (1H, s, broad), 1.60 (1H, s, broad), 1.84 (4H, s, broad), 3.02 (3H, s), 3.39-3.42 (4H, m), 3.64 (2H, s), 4.50-4.83 (8H, m), 5.78 (2H, s), 7.55-7.57 (2H, m), 7.74-7.76 (2H, m), 7.83-7.85 (2H, m), 7.90-7.92 (2H, m), 8.33-8.38 (4H, m).

Example 16 Preparation of Compound 16

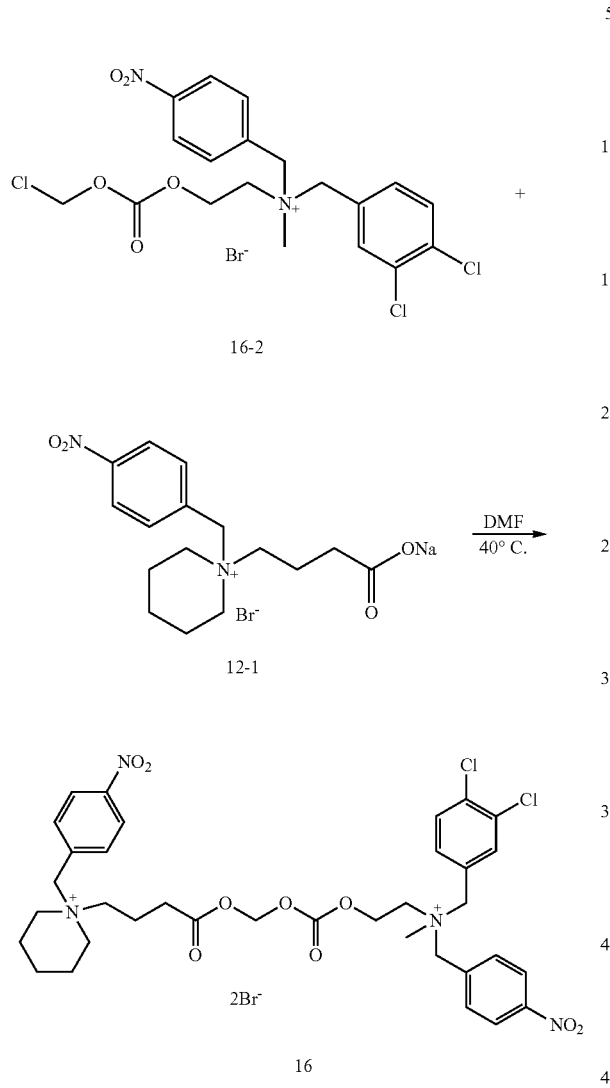

Intermediates 12-1 and 16-2 can be prepared by referring to the preparative method of the intermediate in Example 1. In order to ensure that the anion is Br', benzyl bromide reagent and hydrobromic acid were used to replace benzyl chloride reagent and dilute hydrochloric acid in Example 1 when preparing intermediates 12-1 and 16-2. Intermediate 12-1 (2.04 g) and intermediate 16-2 (2.71 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (1.18 g), i.e. compound 16, with a yield of 26.4%.

$^1$HNMR (400 MHz, DMSO-$d_6$) δ: 1.45 (1H, s, broad), 1.61-1.64 (1H, m), 1.84 (4H, s, broad), 2.10 (2H, s, broad), 2.58-2.61 (2H, m), 3.07 (3H, s), 3.25-3.44 (6H, m), 3.71 (2H, s, broad), 4.56-4.77 (6H, m), 4.90-5.04 (2H, m), 5.79 (2H, s), 7.65-7.96 (7H, m), 8.33-8.39 (4H, m).

Example 17 Preparation of Compound 17

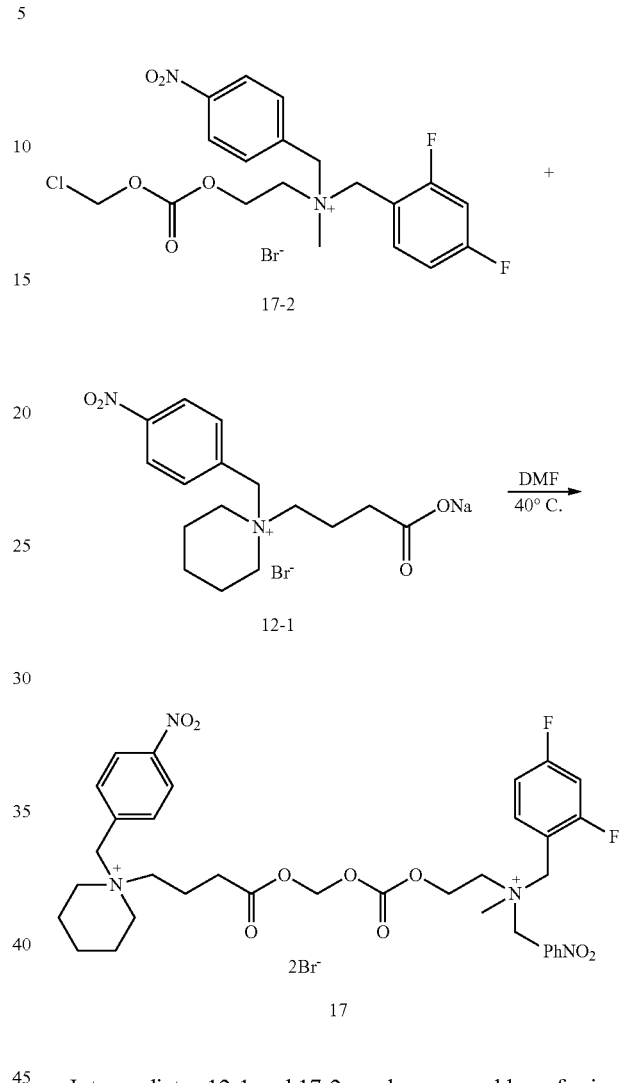

Intermediates 12-1 and 17-2 can be prepared by referring to the preparative method of the intermediate in Example 1. In order to ensure that the anion is Br', benzyl bromide reagent and hydrobromic acid were used to replace benzyl chloride reagent and dilute hydrochloric acid in Example 1 when preparing intermediates 12-1 and 17-2. Intermediate 12-1 (2.04 g) and intermediate 17-2 (2.55 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (1.02 g), i.e. compound 17, with a yield of 23.7%.

$^1$HNMR (400 MHz, DMSO-$d_6$) δ: 1.42 (1H, s, broad), 1.59 (1H, s, broad), 1.83 (4H, s, broad), 2.08 (2H, s, broad), 2.56-2.59 (2H, m), 3.04 (3H, s), 3.23-3.31 (4H, m), 3.40-3.43 (2H, m), 3.63-3.79 (2H, m), 4.51-4.54 (1H, d, J=12 Hz), 4.76-4.79 (5H, m), 4.89-4.99 (2H, m), 5.77 (2H, s), 7.29-7.31 (1H, m), 7.48-7.51 (1H, m), 7.78-7.86 (3H, m), 7.94-7.96 (2H, m), 8.32-8.38 (4H, m).

Example 18 Preparation of Compound 18

Example 19 Preparation of Compound 19

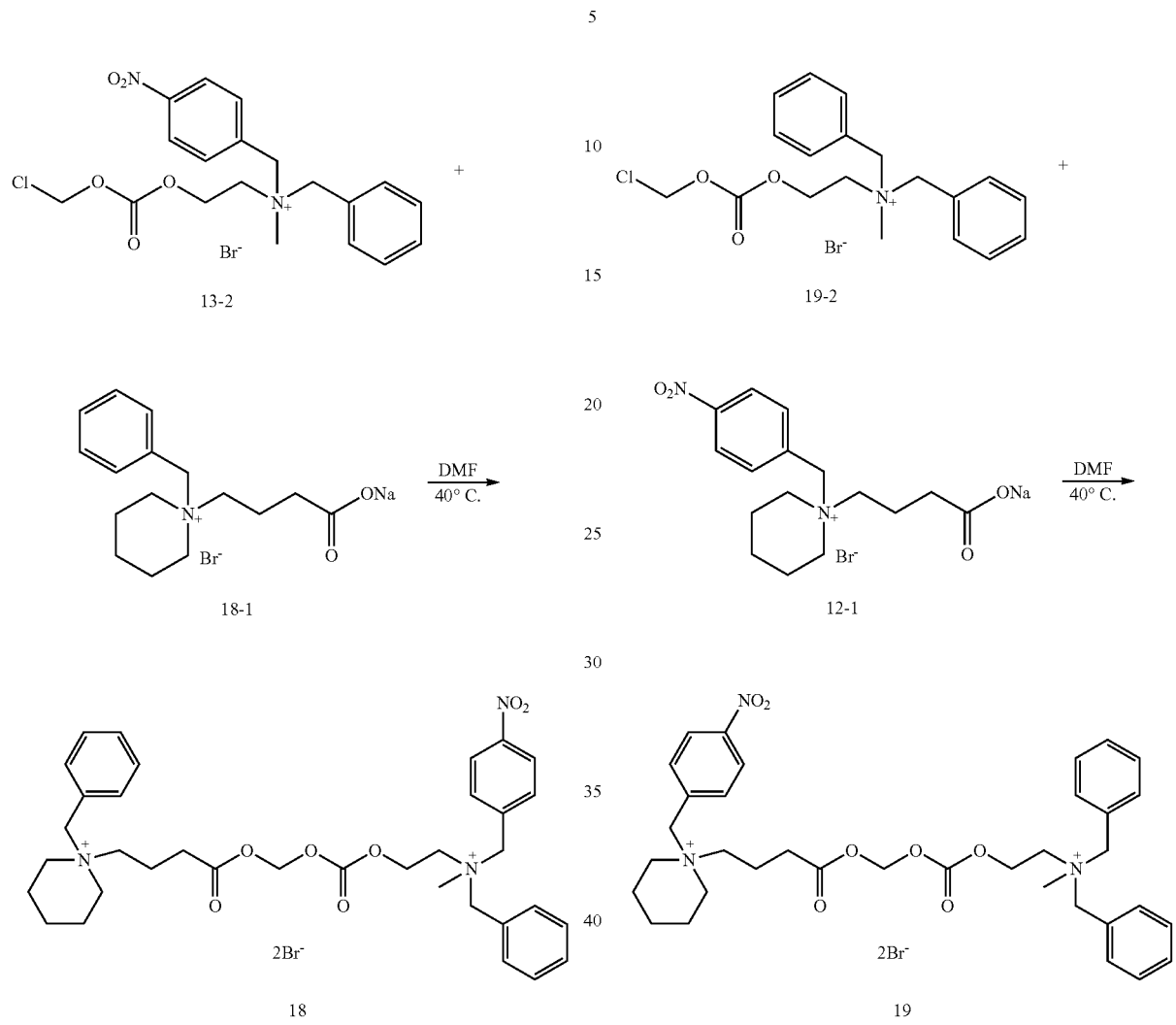

Intermediates 18-1 and 13-2 can be prepared by referring to the preparative method of the intermediate in Example 1. In order to ensure that the anion is Br⁻, benzyl bromide reagent and hydrobromic acid were used to replace benzyl chloride reagent and dilute hydrochloric acid in Example 1 when preparing intermediates 18-1 and 13-2. Intermediate 18-1 (1.82 g) and intermediate 13-2 (2.37 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (0.87 g), i.e. compound 18, with a yield of 22.3%.

$^1$HNMR (400 MHz, DMSO-$d_6$) δ: 1.43-1.46 (1H, m), 1.61-1.64 (1H, m), 1.78-1.90 (4H, m), 2.03-2.12 (2H, m), 2.53-2.59 (2H, m), 3.07 (3H, s), 3.15-3.27 (4H, m), 3.42-3.43 (2H, m), 3.65-3.75 (2H, m), 4.68-4.76 (6H, m), 4.84-4.97 (2H, m), 5.71 (2H, s), 7.50-7.62 (10H, m), 7.83-7.95 (2H, m), 8.31-8.37 (2H, m).

Intermediates 12-1 and 19-2 can be prepared by referring to the preparative method of the intermediate in Example 1. In order to ensure that the anion is Br, benzyl bromide reagent and hydrobromic acid were used to replace benzyl chloride reagent and dilute hydrochloric acid in Example 1 when preparing intermediates 12-1 and 19-2. Intermediate 12-1 (2.04 g) and intermediate 19-2 (2.14 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (0.79 g), i.e. compound 19, with a yield of 20.2%.

$^1$HNMR (400 MHz, DMSO-$d_6$) δ: 1.42-1.46 (1H, m), 1.61-1.65 (1H, m), 1.78-1.91 (4H, m), 2.03-2.11 (2H, m), 2.52-2.58 (2H, m), 3.06 (3H, s), 3.15-3.27 (4H, m), 3.41-3.44 (2H, m), 3.64-3.76 (2H, m), 4.67-4.75 (6H, m), 4.83-4.96 (2H, m), 5.75 (2H, s), 7.51-7.63 (10H, m), 7.82-7.95 (2H, m), 8.33-8.35 (2H, m).

Example 20 Preparation of Compound 20

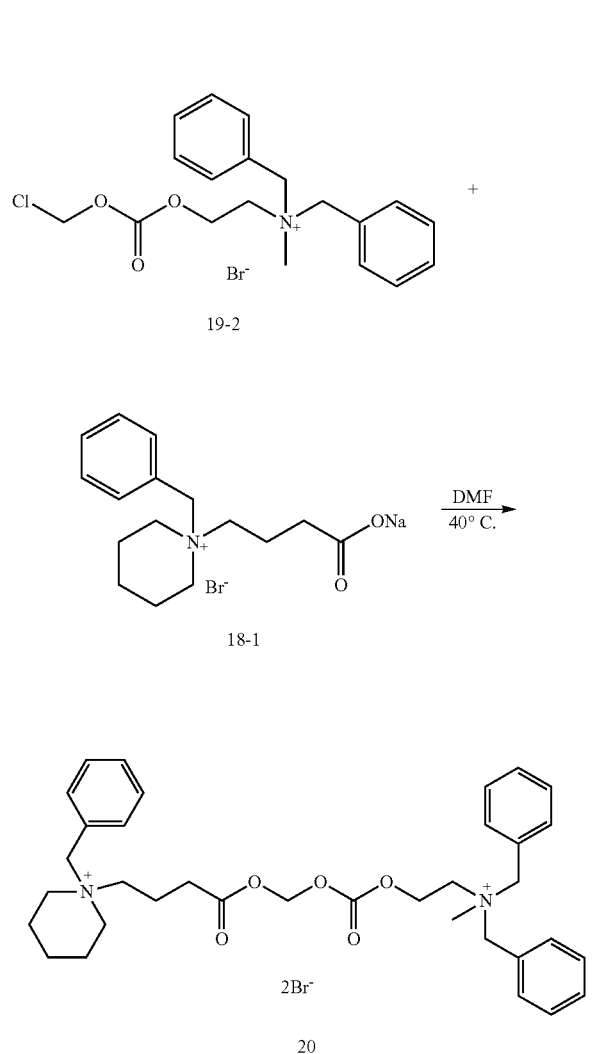

Example 21 Preparation of Compound 21

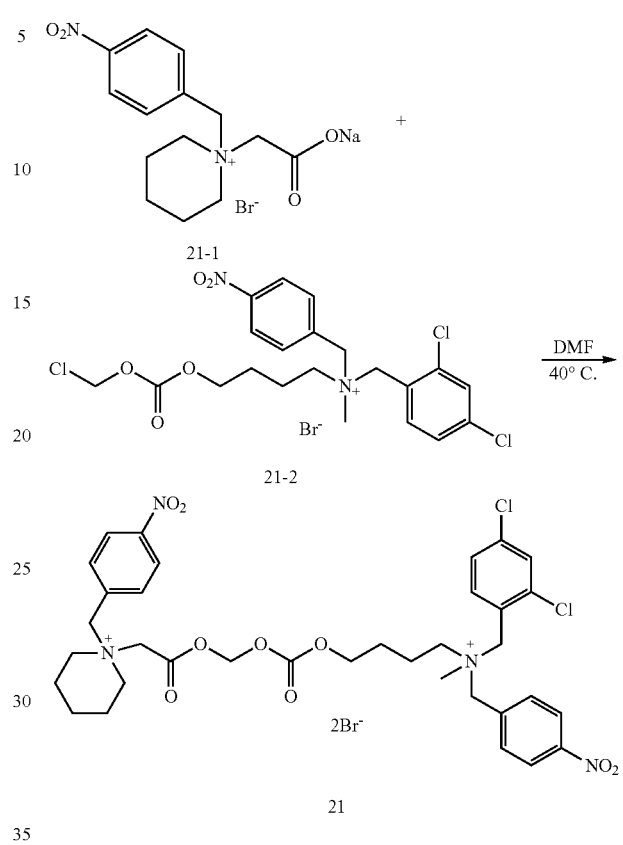

Intermediates 18-1 and 19-2 can be prepared by referring to the preparative method of the intermediate in Example 1. In order to ensure that the anion is Br', benzyl bromide reagent and hydrobromic acid were used to replace benzyl chloride reagent and dilute hydrochloric acid in Example 1 when preparing intermediates 18-1 and 19-2. Intermediate 18-1 (1.82 g) and intermediate 19-2 (2.14 g) were dissolved in 50 mL N,N-dimethylformamide, and the mixture was stirred at 40° C. for 12 h. The solvent was evaporated to dryness under reduced pressure, and the residue was separated by reversed-phase preparative chromatography, to provide white powder (0.79 g), i.e. compound 20, with a yield of 20.1%.

$^1$HNMR (400 MHz, DMSO-$d_6$) δ: 1.41-1.45 (1H, m), 1.60-1.64 (1H, m), 1.77-1.91 (4H, m), 2.02-2.11 (2H, m), 2.51-2.58 (2H, m), 3.09 (3H, s), 3.17-3.27 (4H, m), 3.40-3.46 (2H, m), 3.63-3.78 (2H, m), 4.66-4.75 (6H, m), 4.82-4.96 (2H, m), 5.78 (2H, s), 7.51-7.63 (6H, m), 7.68-7.73 (9H, m).

Quaternary ammonium intermediates 21-1 and 21-2 can be prepared by referring to Example 1. Intermediate 21-1 (2.05 g) and intermediate 21-2 (2.75 g) were dissolved in 50 mL acetonitrile, and the mixture was stirred at 40° C. for 12 h. The solvent was evaporated to dryness under reduced pressure, and the residue was separated by reversed-phase preparative chromatography, to provide white powder (1.16 g), i.e. compound 21, with a yield of 25.1%.

$^1$HNMR (DMSO-de, 400 MHz) δ: 1.43-1.59 (4H, m), 1.67-1.99 (6H, m), 3.01 (3H, s), 3.34-3.39 (2H, m), 3.56-3.59 (2H, m), 3.79-3.82 (2H, m), 4.24 (2H, t, J=8 Hz), 4.57 (2H, s), 4.66-4.78 (3H, m), 4.83-5.00 (3H, m), 5.85 (2H, s), 7.61-7.64 (1H, m), 7.77-7.85 (4H, m), 7.95-7.99 (2H, m), 8.30-8.36 (4H, m).

Example 22 Preparation of Compound 22

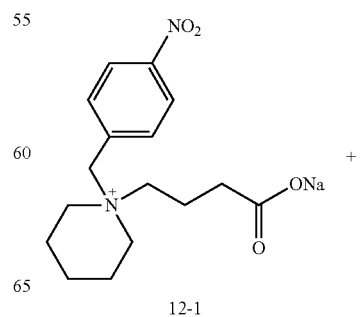

-continued

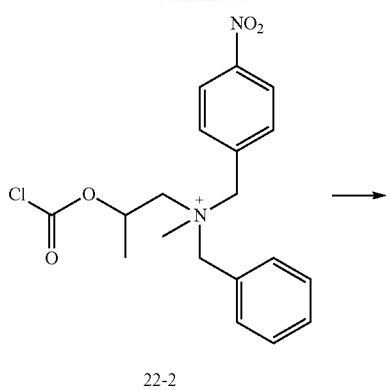

22-2

-continued

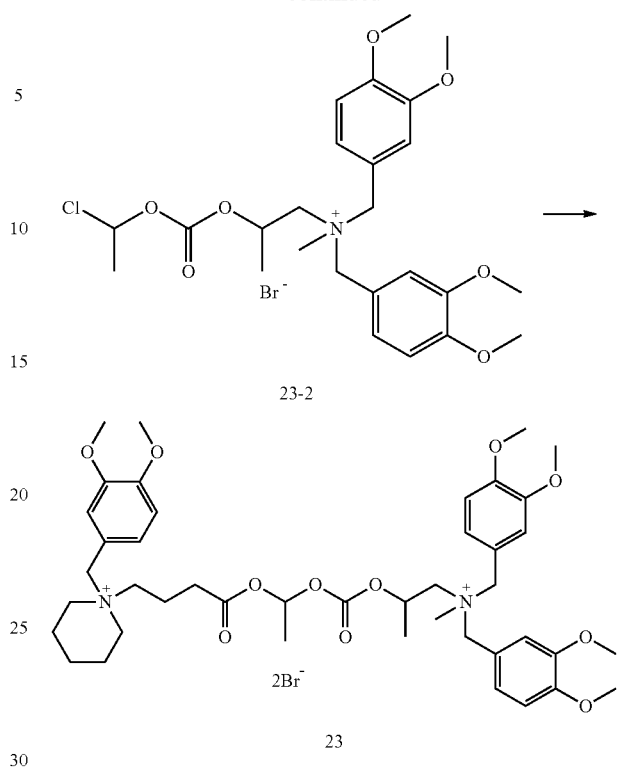

23-2

22

23

Quaternary ammonium intermediates 12-1 and 22-2 can be prepared by referring to Example 1. Intermediate 21-1 (2.05 g) and intermediate 22-2 (2.30 g) were dissolved in 50 mL acetonitrile, and the mixture was stirred at 40° C. for 12 h. The solvent was evaporated to dryness under reduced pressure, and the residue was separated by reversed-phase preparative chromatography, to provide white powder (1.25 g), i.e. compound 22, with a yield of 29.8%.

$^1$HNMR (DMSO-de, 400 MHz) δ: 1.30-1.42 (4H, m), 1.59-1.62 (1H, m), 1.83 (4H, s, broad), 2.08 (2H, s), 2.58 (2H, s), 3.07 (3H, s), 3.30 (4H, s, broad), 3.41-3.73 (4H, m), 4.60-4.62 (1H, s), 4.80 (3H, s, broad), 4.90 (1H, s), 4.99-5.02 (1H, m), 5.26-5.38 (1H, m), 5.72-5.80 (2H, m), 7.52-7.54 (3H, m), 7.65-7.66 (2H, m), 7.86-7.88 (2H, m), 7.99-8.00 (2H, m), 8.32-8.38 (4H, m).

Example 23 Preparation of Compound 23

Quaternary ammonium intermediates 23-1 and 23-2 can be prepared by referring to Example 1. Intermediate 23-1 (2.12 g) and intermediate 23-2 (2.88 g) were dissolved in 50 mL acetonitrile, and the mixture was stirred at 40° C. for 12 h. The solvent was evaporated to dryness under reduced pressure, and the residue was separated by reversed-phase preparative chromatography, to provide white powder (0.91 g), i.e. compound 23, with a yield of 19.3%.

$^1$HNMR (DMSO-d6, 400 MHz) δ: 1.31 (d, J=0.8, 5.6 Hz, 3H), 1.35-1.42 (m, 1H), 1.55-1.60 (m, 4H), 1.83 (s, broad, 4H), 2.08 (s, 2H), 2.56-2.58 (m, 2H), 3.07 (s, 3H), 3.30 (s, broad, 4H), 3.41-3.55 (m, 3H), 3.66-3.73 (m, 1H), 3.79-3.82 (m, 18H), 4.60-4.61 (m, 1H), 4.80 (s, broad, 3H), 4.90-5.02 (m, 2H), 5.26-5.38 (m, 1H), 5.72-5.80 (m, 1H), 7.05-7.26 (m, 9H).

Example 24 Preparation of Compound 24

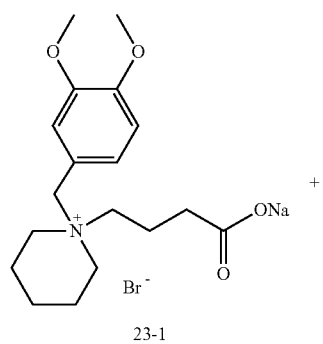

23-1

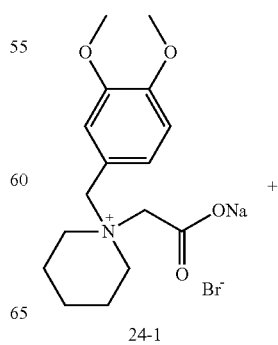

24-1

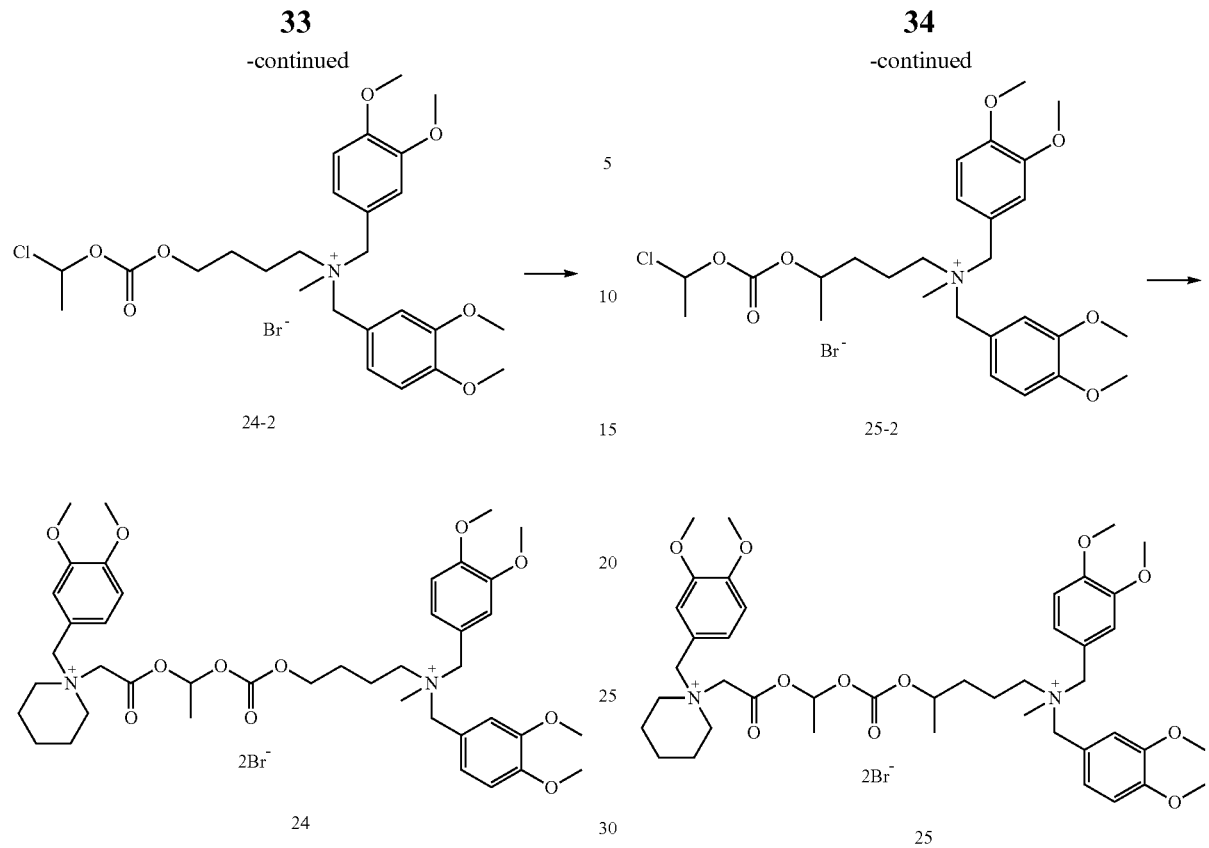

Quaternary ammonium intermediates 24-1 and 24-2 can be prepared by referring to Example 1. Intermediate 24-1 (2.00 g) and intermediate 24-2 (2.95 g) were dissolved in 50 mL acetonitrile, and the mixture was stirred at 40° C. for 12 h. The solvent was evaporated to dryness under reduced pressure, and the residue was separated by reversed-phase preparative chromatography, to provide white powder (0.96 g), i.e. compound 24, with a yield of 20.7%.

$^1$HNMR (DMSO-de, 400 MHz) δ: 1.42-1.60 (m, 5H), 1.62-1.71 (m, 2H), 1.89-2.05 (m, 6H), 3.01 (s, 3H), 3.37 (s, 2H), 3.53-3.63 (m, 2H), 3.79-3.82 (m, 20H), 4.24 (t, J=6.40 Hz, 2H), 4.66-5.00 (m, 8H), 5.85 (m, 1H), 7.09-7.27 (m, 9H).

Example 25 Preparation of Compound 25

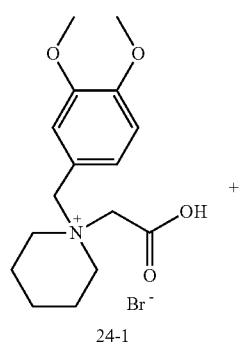

24-1

Quaternary ammonium intermediates 24-1 and 25-2 can be prepared by referring to Example 1. Intermediate 24-1 (2.00 g) and intermediate 25-2 (3.02 g) were dissolved in 50 mL acetonitrile, and the mixture was stirred at 40° C. for 12 h. The solvent was evaporated to dryness under reduced pressure, and the residue was separated by reversed-phase preparative chromatography, to provide white powder (1.07 g), i.e. compound 25, with a yield of 22.7%.

$^1$HNMR (DMSO-de, 400 MHz) δ: 1.30 (d, J=5.6 Hz, 3H), 1.43-1.65 (m, 5H), 1.61-1.73 (m, 2H), 1.87-2.04 (m, 6H), 3.05 (s, 3H), 3.35 (s, 2H), 3.52-3.65 (m, 2H), 3.79-3.82 (m, 20H), 4.26 (t, J=6.4 Hz, 2H), 4.64-5.03 (m, 7H), 5.82 (m, 1H), 7.04-7.25 (m, 9H).

The beneficial effect of the present invention was illustrated by an experimental example.

Experimental Example 1

Male New Zealand white rabbits weighing 2-3.5 kg were used as experimental animals for muscle relaxation test. The specific procedures were as follows: propofol emulsion was used to induce and maintain general anesthesia (induction dose: 10 mg/kg; maintenance dose: 105 mg/hr/kg). Tracheal intubation was carried out and respiratory support was used. After 2×ED$_{95}$ equivalent dose of the control drug and the compounds described in the present patent were intravenously injected, the onset time (TOF=0) of the drug and the recovery time (TOF=90%) of muscle relaxation were observed with a neuromuscular transmission monitors (TOF). The results are shown in Table 1.

TABLE 1

The onset time and the duration of muscle relaxant action of drugs in rabbits

| Drug | 2 × $ED_{95}$ (mg/kg) | Onset time (s) | Recovery time (min) |
| --- | --- | --- | --- |
| Cisatracurium | 0.08 | >120 | 17.6 ± 3.2 |
| Succinylcholine | 1.8 | <40 | 12.3 ± 4.1 |
| Compound 1 | 0.5 | <40 | 4.2 ± 1.1 |
| Compound 2 | 1.4 | <40 | 5.4 ± 1.2 |
| Compound 3 | 1.3 | <40 | 3.8 ± 0.4 |
| Compound 4 | 0.4 | <40 | 4.4 ± 0.5 |
| Compound 5 | 0.4 | <40 | 6.2 ± 1.4 |
| Compound 6 | 0.9 | <40 | 5.1 ± 2.1 |
| Compound 7 | 1.2 | <40 | 5.2 ± 2.1 |
| Compound 8 | 1.2 | <40 | 7.2 ± 1.8 |
| Compound 9 | 0.6 | <40 | 4.2 ± 1.1 |
| Compound 10 | 0.7 | <40 | 4.2 ± 0.9 |
| Compound 11 | 0.5 | <40 | 6.7 ± 2.6 |
| Compound 12 | 1.8 | <40 | 8.1 ± 0.2 |
| Compound 13 | 2.1 | <40 | 7.9 ± 1.9 |
| Compound 14 | 2.4 | <40 | 4.2 ± 1.2 |
| Compound 15 | 1.9 | <40 | 5.3 ± 2.1 |
| Compound 16 | 2.2 | <40 | 5.2 ± 1.1 |
| Compound 17 | 1.8 | <40 | 3.1 ± 0.3 |
| Compound 18 | 1.9 | <40 | 7.2 ± 2.7 |
| Compound 19 | 2.2 | <40 | 7.1 ± 1.2 |
| Compound 20 | 2.4 | <40 | 6.9 ± 2.5 |
| Compound 21 | 4.0 | <40 | 5.1 ± 1.1 |
| Compound 22 | 1.2 | <40 | 6.2 ± 1.4 |
| Compound 23 | 1.2 | <40 | 7.8 ± 2.4 |
| Compound 24 | 1.4 | <40 | 8.4 ± 1.9 |
| Compound 25 | 1.4 | <40 | 8.1 ± 2.9 |

Above results showed that the compound of the present invention could rapidly produce muscle relaxation in animals (<40 seconds), and the continuous time of muscle relaxation was significantly shorter than that of cisatracurium, even shorter than that of succinylcholine. These characteristics showed that the compounds of the present invention had the characteristics of rapid onset and rapid recovery. In addition, after the compound of the present invention was administrated, the TOF 1-4 of the tested animals gradually decreased, rather than in equal proportion. The change characteristics of TOF indicate that the compound in the present invention belongs to a typical non-depolarizing muscle relaxant.

The invention claimed is:

1. A bisquaternary ammonium compound of formula (I):

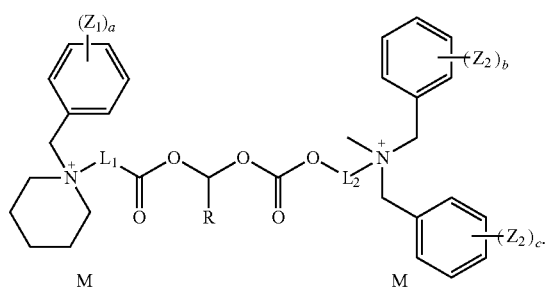

(I)

wherein $L_1$ is $C_1$-$C_8$ alkylenyl, $L_2$ is $C_1$-$C_8$ alkylenyl, $Z_1$ is nitro or halogen or methoxyl, $Z_2$ is nitro or halogen or methoxyl, $Z_3$ is nitro or halogen or methoxyl, R is hydrogen or $C_1$-$C_6$ alkyl, each of a, b, and c is independently selected from 0, 1, 2, 3, 4, and 5, and M is a pharmaceutically acceptable anion.

2. The compound according to claim 1, wherein $Z_1$, $Z_2$, and $Z_3$ are fluorine.

3. The compound according to claim 1, wherein $Z_1$, $Z_2$, and $Z_3$ are chlorine, and each of a, b, and c is independently selected from 0, 1, and 2.

4. The compound according to claim 1, wherein $Z_1$, $Z_2$, and $Z_3$ are nitro, and each of a, b, and c is independently selected from 0, 1, and 2.

5. The compound according to claim 1, wherein $Z_1$, $Z_2$, and $Z_3$ are bromine, and each of a, b, and c is independently selected from 0, 1, and 2.

6. The compound according to claim 1, wherein $Z_1$, $Z_2$, and $Z_3$ are methoxyl, and each of a, b, and c is independently selected from 0, 1, and 2.

7. The compound according to claim 1, wherein R is hydrogen or methyl.

8. The compound according to claim 1, wherein said compound is selected from

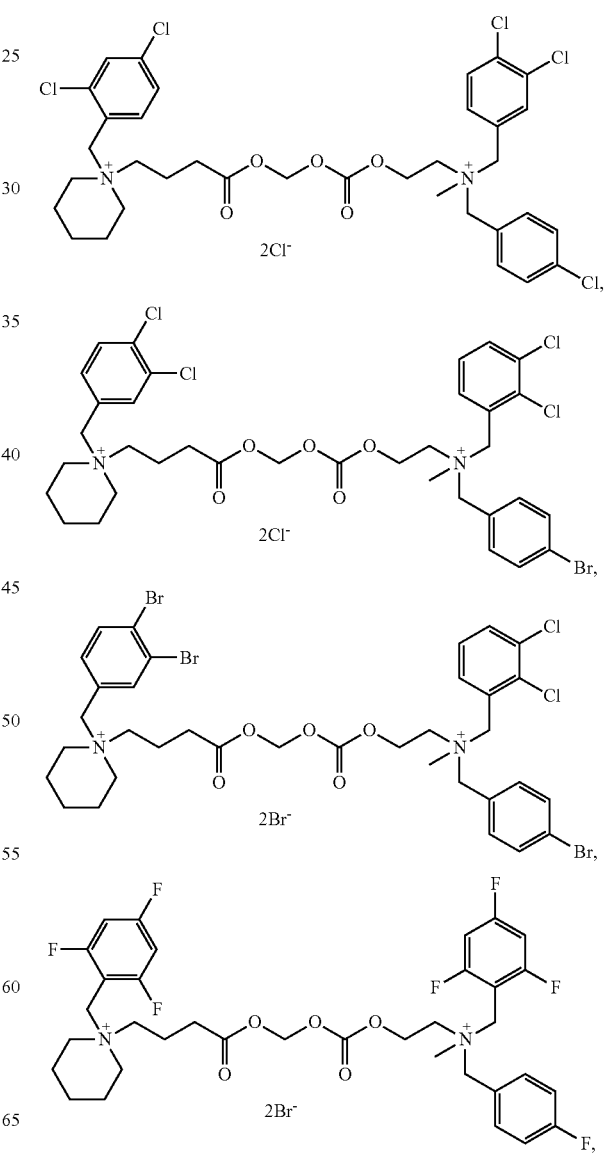

-continued
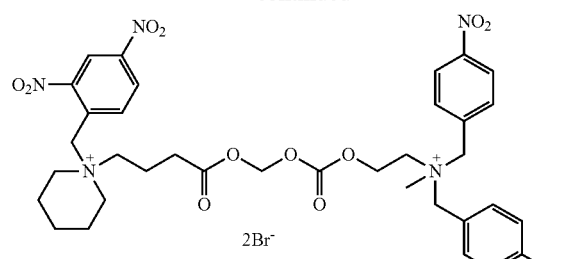
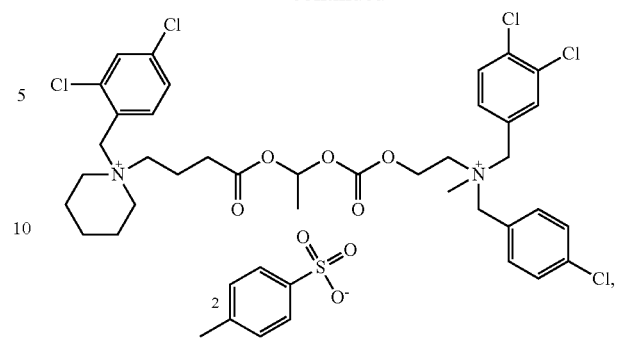
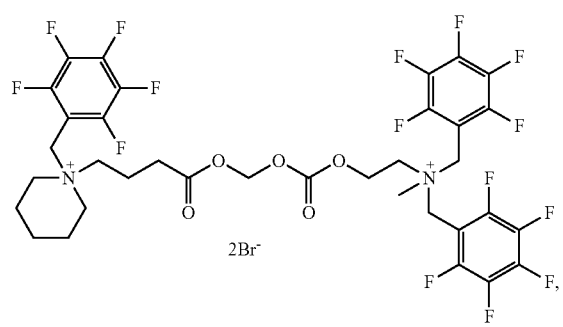
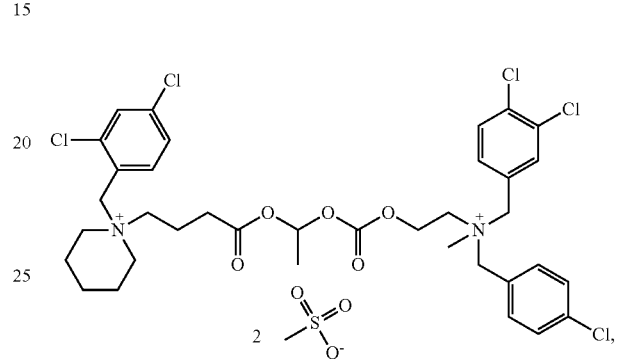
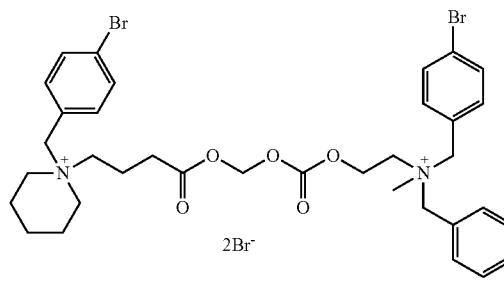
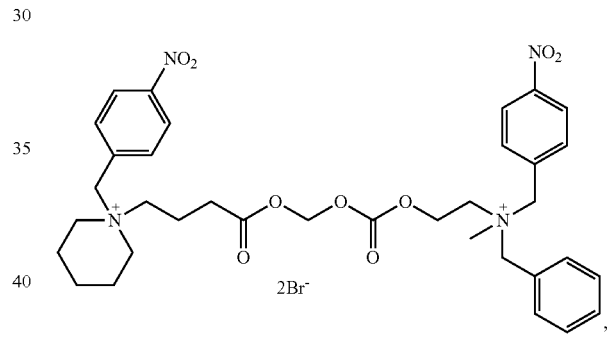
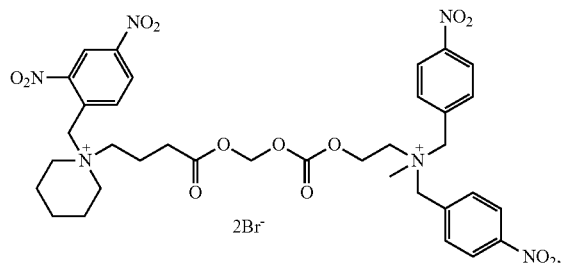
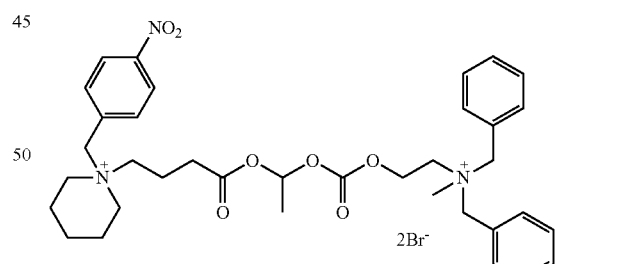
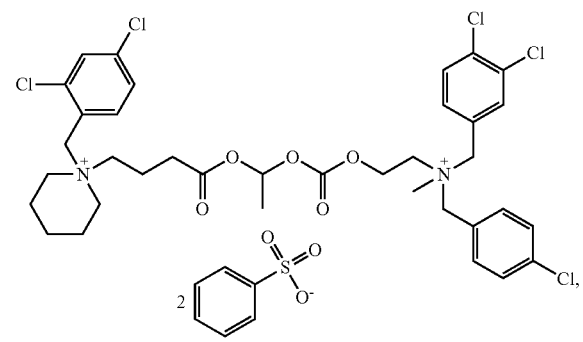
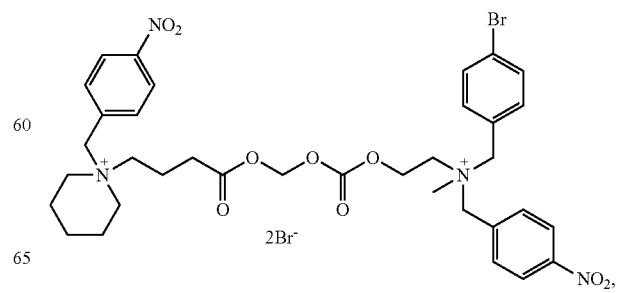

-continued

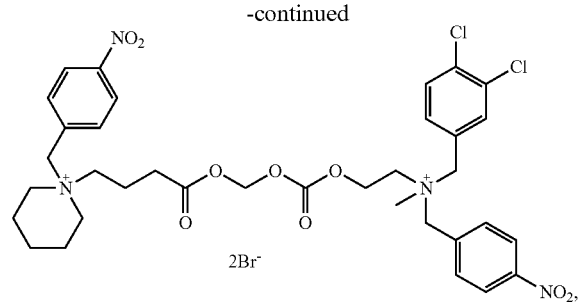

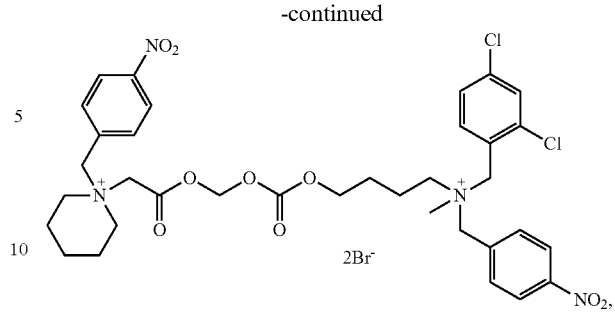

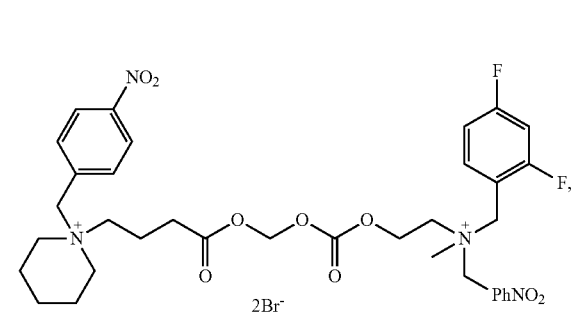

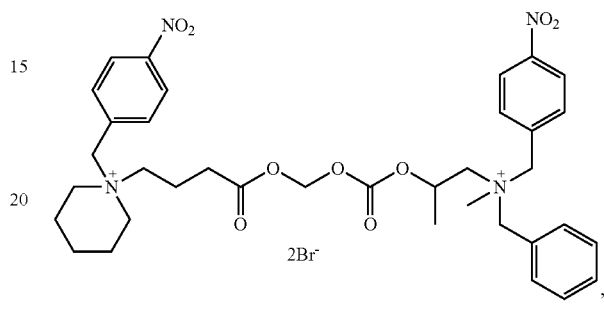

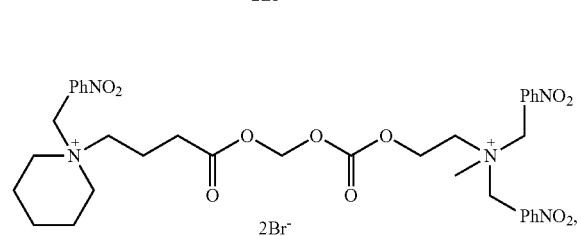

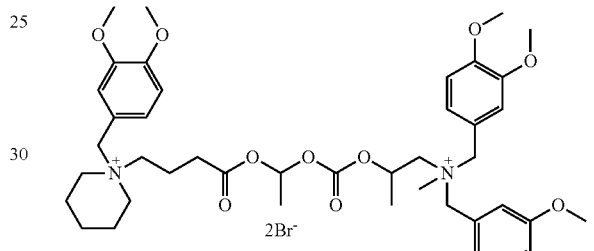

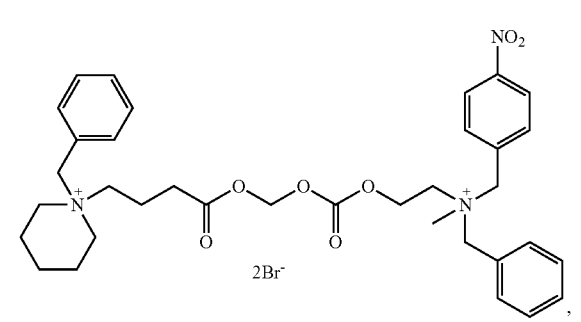

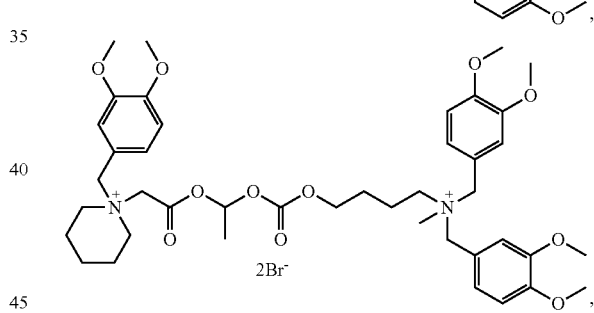

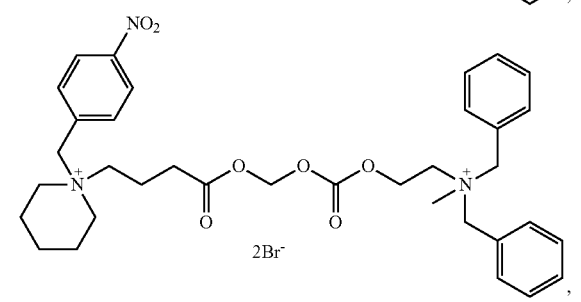

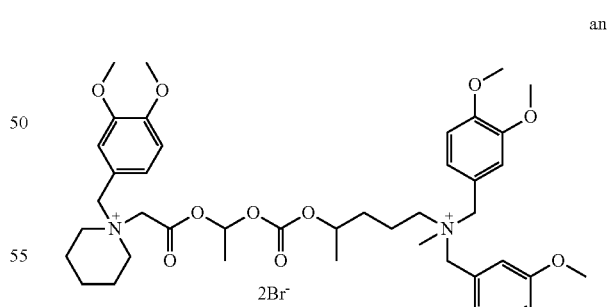

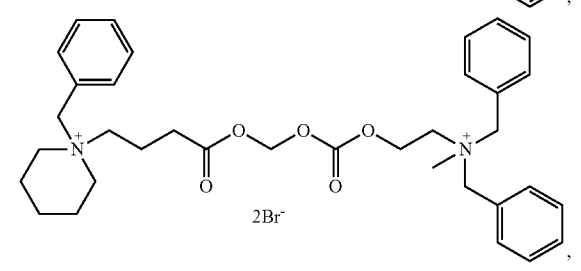

and

9. A muscle relaxant comprising the bisquaternary ammonium compound according to claim 1 as an active ingredient and a pharmaceutically acceptable adjuvant.

10. A method for preparing a muscle relaxant, comprising mixing an active ingredient and a pharmaceutically acceptable adjuvant, wherein the active ingredient is one or more selected from the bisquaternary ammonium compound according to claim 1, stereoisomers thereof, pharmaceutically acceptable salts thereof, solvates thereof, and crystals thereof.

* * * * *